United States Patent
Harmer et al.

(10) Patent No.: US 9,289,564 B2
(45) Date of Patent: Mar. 22, 2016

(54) BLISTER PIERCING ELEMENT FOR DRY POWDER INHALER

(75) Inventors: Quentin John Harmer, Waterbeach (GB); Roger William Clarke, Histon (GB); Stephen William Eason, Redgrave Diss (GB); Andreas Mark Meliniotis, Cambridge (GB)

(73) Assignee: Vectura Delivery Devices Limited, Chippenham (GB)

( * ) Notice: Subject to any disclaimer, the term of this patent is extended or adjusted under 35 U.S.C. 154(b) by 1531 days.

(21) Appl. No.: 11/919,817

(22) PCT Filed: Apr. 13, 2006

(86) PCT No.: PCT/EP2006/061607
§ 371 (c)(1),
(2), (4) Date: Dec. 26, 2007

(87) PCT Pub. No.: WO2006/108877
PCT Pub. Date: Oct. 19, 2006

(65) Prior Publication Data
US 2009/0090362 A1    Apr. 9, 2009

(30) Foreign Application Priority Data

Apr. 15, 2005  (GB) .................................. 0507711.0

(51) Int. Cl.
*A61M 15/00* (2006.01)
(52) U.S. Cl.
CPC ....... *A61M 15/0045* (2013.01); *A61M 15/0033* (2014.02); *A61M 15/0051* (2014.02)
(58) Field of Classification Search
CPC ..................... A61M 15/0028; A61M 15/0045; A61M 2015/0033; A61M 2015/0035; A61M 2015/0036; A61M 2015/0038; A61M 2015/004; A61M 2015/0041; A61M 2202/064
USPC ............ 128/200.21, 203.12, 203.15, 203.21, 128/203.23, 203.24; 222/80; 604/23, 24, 604/26, 57, 58, 272–274; 141/329, 19; 37/24, 452, 446, 454; 30/358–368
See application file for complete search history.

(56) References Cited

U.S. PATENT DOCUMENTS 4,627,432 A    12/1986 Newell et al.
4,678,106 A     7/1987 Newell et al.
(Continued)

FOREIGN PATENT DOCUMENTS

DE    19502725    8/1996    ............. B65D 47/00
EP    0129985 A1   1/1985
(Continued)

OTHER PUBLICATIONS

Search report issued by the National Center of the Intellectual Property "Sakpatent" of Georgia for corresponding Georgian Patent Application No. AP2006010373.
(Continued)

*Primary Examiner* — Justine Yu
*Assistant Examiner* — LaToya M Louis
(74) *Attorney, Agent, or Firm* — Davidson, Davidson & Kappel LLC

(57) ABSTRACT

A blister piercing element for puncturing the lid of a blister containing a dose of medicament for inhalation by a user. The piercing element has an outlet opening for the passage of medicament entrained in an airflow out of the blister and, a piercing head extending beyond and overhanging the opening that cuts a flap in a lid of a blister and pushes it away from the opening during insertion.

7 Claims, 21 Drawing Sheets

(56) References Cited

U.S. PATENT DOCUMENTS

| | | | |
|---|---|---|---|
| 4,811,731 A | 3/1989 | Newell et al. | |
| 4,826,492 A | 5/1989 | Magasi | |
| 5,035,237 A | 7/1991 | Newell et al. | |
| 5,312,422 A * | 5/1994 | Trott | 606/144 |
| 5,533,502 A | 7/1996 | Piper | 128/203.21 |
| 5,542,411 A | 8/1996 | Rex | 128/203.15 |
| 5,617,971 A | 4/1997 | Eason et al. | 221/31 |
| 5,769,073 A | 6/1998 | Eason et al. | |
| 5,785,049 A | 7/1998 | Smith et al. | |
| 5,848,996 A * | 12/1998 | Eldor | 604/272 |
| 5,875,776 A * | 3/1999 | Vaghefi | 128/203.15 |
| 5,881,719 A | 3/1999 | Gottenauer et al. | |
| 6,089,228 A | 7/2000 | Smith et al. | 128/203.15 |
| 6,401,712 B1 | 6/2002 | Von Schuckmann | 128/203.15 |
| 6,543,448 B1 | 4/2003 | Axford et al. | 128/203.15 |
| 6,637,431 B2 | 10/2003 | Ekelius et al. | 128/203.15 |
| 6,732,732 B2 * | 5/2004 | Edwards et al. | 128/203.21 |
| 7,070,583 B1 * | 7/2006 | Higuchi et al. | 604/274 |
| 7,651,482 B2 * | 1/2010 | Harris | 604/272 |
| 7,950,389 B2 | 5/2011 | Eason et al. | |
| 2001/0029948 A1 * | 10/2001 | Ingle et al. | 128/203.15 |
| 2004/0154619 A1 | 8/2004 | Edwards et al. | 128/203.15 |
| 2004/0236282 A1 | 11/2004 | Braithwaite | |
| 2005/0161041 A1 | 7/2005 | Schuler et al. | |
| 2006/0185672 A1 | 8/2006 | Pinon et al. | |
| 2006/0200095 A1 * | 9/2006 | Steube | 604/272 |
| 2006/0212004 A1 * | 9/2006 | Atil | 604/272 |
| 2006/0254583 A1 * | 11/2006 | Deboeck et al. | 128/203.15 |
| 2007/0074721 A1 | 4/2007 | Harmer et al. | |
| 2009/0090362 A1 | 4/2009 | Harmer et al. | |
| 2010/0108058 A1 | 5/2010 | Glusker et al. | |
| 2010/0192949 A1 | 8/2010 | Wright et al. | |
| 2011/0120463 A1 | 5/2011 | Esteve et al. | |

FOREIGN PATENT DOCUMENTS

| | | | |
|---|---|---|---|
| EP | 0491426 A1 | 6/1992 | |
| EP | 0525720 A1 | 2/1993 | |
| EP | 1132104 | 9/2001 | A61M 15/00 |
| EP | 2082769 A1 | 7/2009 | |
| EP | 2210638 B1 | 3/2013 | |
| GB | 1472650 | 5/1977 | |
| GB | 2246299 A | 1/1992 | |
| GB | 2264237 A | 8/1993 | |
| GB | 2340758 | 3/2000 | A61M 15/00 |
| GB | 2407042 | 4/2005 | A61M 15/00 |
| GB | 2420982 A | 6/2006 | |
| GB | 2439204 A | 12/2007 | |
| JP | A-62-281959 A | 12/1987 | |
| JP | 05200100 A | 8/1993 | |
| JP | 2009-510367 A | 10/1997 | |
| JP | A-2002-248094 A | 9/2002 | |
| JP | 2005-509460 A | 4/2005 | |
| JP | 2006-502759 A | 1/2006 | |
| JP | 2006-508699 A | 6/2006 | |
| RU | 2091088 | 9/1997 | A61M 15/00 |
| RU | 2146153 | 3/2000 | A61M 15/00 |
| RU | 2148417 | 5/2000 | A61M 15/00 |
| RU | 2158609 C1 | 11/2000 | |
| WO | WO 9013328 A1 | 11/1990 | |
| WO | WO 9106333 | 5/1991 | A61M 15/00 |
| WO | WO 9506491 A2 | 3/1995 | |
| WO | WO 9531238 | 11/1995 | A61M 15/00 |
| WO | WO 9609085 | 3/1996 | A61M 15/00 |
| WO | 0126720 | 4/2001 | A61M 15/00 |
| WO | WO01/43802 A1 | 6/2001 | |
| WO | 0185097 | 11/2001 | |
| WO | 0187393 | 11/2001 | A61M 15/00 |
| WO | WO 0202161 A1 * | 1/2002 | |
| WO | WO03080163 A1 | 10/2003 | |
| WO | 2005025656 | 3/2005 | A61M 15/00 |
| WO | 2005037353 | 4/2005 | A61M 15/00 |
| WO | WO2006/108877 A2 | 10/2006 | |
| WO | WO2007/098870 A1 | 9/2007 | |
| WO | WO2008/051621 A2 | 5/2008 | |
| WO | WO2009/004465 A1 | 1/2009 | |

OTHER PUBLICATIONS

International Search Report, dated May 2, 2001, issued in connection with corresponding International Application WO 2001/026720.

Japanese Office action in connection with Japanese application No. 2008-505906, dated Jul. 13, 2011.

* cited by examiner

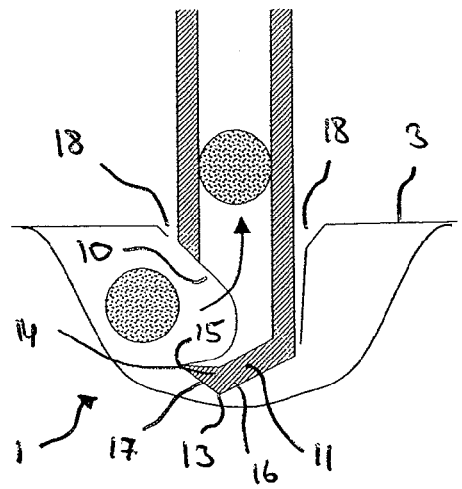
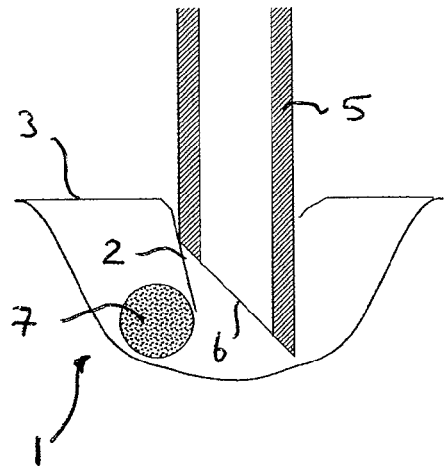
FIGURE 3
FIGURE 4 (PRIOR ART)
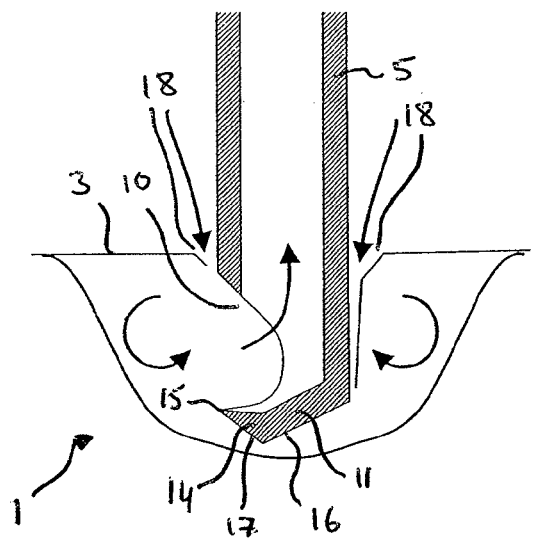
FIGURE 5

BLISTER PIERCING ELEMENT FOR DRY POWDER INHALER

This application is a U.S. national phase application of International application No. PCT/EP2006/061607, filed Apr. 13, 2006, which claims priority to GB 0507711.0, filed Apr. 15, 2005.

FIELD OF THE INVENTION

The present invention relates to a piercing element for a dry powder inhalation device. In particular, it relates to a piercing element for puncturing the foil lid of a blister that contains an individual dose of medicament for inhalation by a user of the inhalation device.

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs, thereby avoiding the need for hypodermic injections.

It is common for dry powder formulations to be pre-packaged in blisters each of which contain a single dose of powder which has been accurately and consistently measured. The foil blister protects each dose from the ingress of moisture and penetration of gases such as oxygen in addition to shielding the dose from light and UV radiation all of which can have a detrimental effect on the medicament and on the operation of an inhaler used to deliver the medicament to a patient.

A blister pack generally comprises a base having one or more spaced apart cavities defining blisters to receive individual doses of medicament and, a lid in the form of a generally planar sheet that is sealed to the base except in the region of the cavities. The base material is typically a laminate comprising a polymer layer in contact with the drug, a soft tempered aluminium layer and an external polymer layer. The aluminium provides the moisture and oxygen barrier, whilst the polymer aids adhesion of the aluminium to the heat seal lacquer and provides a relatively inert layer in contact with the drug. Soft tempered aluminium is ductile so that it can be "cold formed" into a blister shape. It is typically 45 μm thick. The outer polymer layer provides additional strength and toughness to the laminate.

The lid material is typically a laminate comprising a heat seal lacquer, a hard rolled aluminium layer and an external lacquer layer. The heat seal lacquer layer bonds to the polymer layer of the base foil laminate during heat-sealing to provide a seal around the top of the blister cavity. The hard temper foil is relatively frangible to enable it to be pierced easily by a piercing element forming part of an inhalation device, to create one or more openings in the lid. These openings enable air or gas to flow through the blister, thereby entraining the dry powder and causing it to be removed from the blister. The powder can then be deagglomerated to form a respirable cloud and made available for inhalation by the user.

Inhalation devices that receive a blister pack or strip of blisters are known. Actuation of the device causes a mechanism to index and pierce a blister so that when the device is used, air is drawn through the blister entraining the dose, which is then carried out of the blister through the device and via the patient's airway down into the lungs. One such device is known from the Applicant's co-pending international application no. PCT/GB2004/004416 which has now been published as WO 2005/037353 A1.

The airflow can be created by inhalation of the user. Such inhaler devices are generally known as passive devices. Alternatively, the inhaler may include a source of energy such as a mechanical pump or canister of pressurised gas to generate pressure or suction. The air or gas flow in these active devices can potentially be greater than that in a passive device, and more repeatable. This can give better and more consistent blister emptying.

It has been found that it is difficult to control the size and configuration of the opening that is pierced in a blister lid because the foil may not always tear or burst in a consistent way. However, the means by which the blister is pierced is of critical importance in the performance of a dry powder inhalation device.

It is common for problems to occur because, when the lid is pierced, foil flaps are formed that are pushed into the blister. These can either trap powder in the blister or obscure the opening. It will be appreciated that it is beneficial to form a large opening in the blister lid to enable a sufficient flow of air through the blister, and to enable the removal of agglomerates that may have formed in the powder during storage. However, a large opening in the blister means that the foil flaps are large and so are more likely to trap powder and hinder airflow.

Many conventional devices use a piercing element that remains in the blister during inhalation rather than being withdrawn. U.S. Pat. No. 5,533,502 and GB2340758 disclose devices that have two piercing elements that enter the blister or dose container. The piercing elements are of a hollow tubular form with a bevelled end to facilitate piercing. The air or gas flows into the blister through one piercing element and leaves through another. However, a disadvantage with the piercing elements in these devices is that the small size of the gas conduit can significantly restrict gas flow through the blister, particularly with a passive device, and also prevent the removal of agglomerates. Further, the foil flap that is formed by the bevelled end can obstruct the opening in the piercing element. This requires the piercing element to be pushed further into the blister than would otherwise be necessary.

The process by which a foil flap is formed in a blister lid by a piercing element having a bevelled end is shown in FIG. 1A to 1D, from which it will be appreciated that the foil flap partially blocks the air flow path through the tube (see FIGS. 1(b) and 1(c)) unless inserted deep into the blister (see FIG. 1(d)). U.S. Pat. No. 6,401,712 and U.S. Pat. No. 6,637,431 both disclose devices in which a suction tube is inserted into a foil blister. However, in both cases the suction tube and the cut foil flaps create a significant intrusion into the foil blister.

An attempt to mitigate the problems described above is provided by the device disclosed in WO01/87393, which has a piercing element comprising a central exit and peripheral inlets. The piercing element rotates as it is inserted so that the cut portions of the lidding foil curl upwards out of the blister rather than into it. Although this has the benefit of reducing intrusion of cut foil flaps into the blister, improving gas flow and reducing potential for trapping drug, the mechanism for causing the piercing element to rotate during insertion makes the device significantly more complex.

The Applicant's own earlier applications PCT/GB2004/03940 and PCT/GB2004/004416, published as WO 2005/025656 A1 and WO 2005/037353 A1, respectively, also propose improvements in blister piercing and emptying. PCT/GB2004/03940 discloses a drug outlet tube incorporating a piercing element for cutting a central opening in the blister and, a second piercing element that creates multiple inlet openings around the periphery of the drug outlet tube. However, although the active device disclosed in this document generates sufficient energy to create gas velocities high enough to give efficient scouring of the blister, the drug outlet tube may still be partially obstructed by the foil flap, as previously described, thereby preventing agglomerates that are too large to pass through the remaining gap from leaving the blister.

It is also known from PCT/GB2004/004416 to provide a piercing element with two piercing heads for forming an inlet and an outlet to the blister. Each piercing head comprises a primary blade and two lateral secondary blades that together form an 'H'-shaped configuration. These blades cut and form several foil flaps as the piercing heads are pushed into the foil lid of the blister. This arrangement creates large openings in the lid, enabling a free flow of air through the blister which is of particular benefit to a passive inhalation device such as the device disclosed in this application, in which the suction and flow volume are limited to that which can be created by the user's inhalation.

Although the size of the foil flaps created in the lid of a blister are greatly reduced using a piercing elements referred to above and described in more detail in PCT/GB2004/004416, the foil flaps can still project some way into the blister. Although this is perfectly acceptable if the medicament is in the form of a free-flowing powder, agglomerations of a cohesive powder can still become trapped between the foil flaps and the blister base.

The present invention seeks to overcome or alleviate the problems with the conventional devices described above and other problems associated with the evacuation of a powdered formulation from a blister.

According to the invention, there is provided a blister piercing element for puncturing the lid of a blister containing a dose of medicament for inhalation by a user, the piercing element comprising an outlet opening for the passage of medicament entrained in an airflow out of the blister and, a piercing head extending beyond and overhanging the opening that cuts a flap in a lid of a blister and pushes it away from the opening during insertion.

The piercing head preferably extends from a portion of the periphery of the outlet opening.

It will be appreciated that the piercing head that continues beyond the opening in the tube cuts the foil to form a flap which is then folded back by said piercing head so that it lies against piercing head and does not interfere with the opening, thereby creating a larger passage through the blister than is possible with a conventional piercing head such as one provided with a bevelled end to facilitate piercing.

In a preferred embodiment, the piercing head overhangs the entire outlet opening.

Preferably, the piercing head includes a cutting edge which may be formed at the end of the piercing head.

In one embodiment, the piercing tip is formed proximal to the end of the piercing head. In this case, the end of the piercing member that extends beyond the piercing edge may be angled back towards the opening. The piercing member therefore takes the form of a generally hook shaped element.

In a preferred embodiment, the piercing head is configured such that the cutting edge is angled relative to the plane of a blister lid to be pierced such that only a tip of the cutting edge initially meets the blister lid to initiate a slit in the lid.

A portion of the cutting edge remote from the tip may be chamfered or otherwise removed.

The piercing head may take the form of a blade-like element and the cutting edge may comprise a primary cutting edge formed at the free end of the blade element for cutting an initial slit in a blister lid, wherein a secondary cutting edge extends along either side of the blade element between the primary cutting edge and the outlet for cutting slits in a blister lid substantially at right angles to the incision made by the primary cutting edge to form a flap which is pushed into the blister by the piercing head.

In one embodiment, the blade like element is solid. However, it may also have at least one aperture therein.

In a modified embodiment, a region extending between the secondary cutting edge and the outlet is enclosed by a wall.

In a particularly preferred embodiment, the blister piercing element includes an inlet opening, in addition to the outlet opening, and a pair of piercing heads, one piercing head extending beyond and overhanging the outlet opening and the other piercing head extending beyond and overhanging the inlet opening.

Preferably, the two piercing heads are in a back-to-back orientation. Although they are spaced from each other in a first direction, they may also be spaced from each other or offset from each other in a lateral direction at right angles to the spacing between them.

Preferably, the cutting edge of each piercing head is angled so that the cutting tip initiates a incision close to the centre of a blister lid and cutting edges cut a slit in the blister lid in opposite outwardly extending directions towards opposite edges of the blister lid.

According to another aspect of the invention, there is provided a blister piercing head for puncturing a lid of a blister containing a dose of medicament for inhalation by a user, the blister piercing head comprising a primary cutting element which is configured to cut, as the piercing member enters a blister, a first linear slit in the lid and, secondary cutting elements that extend across each end of the primary cutting element which are configured to cut, as the piercing head enters a blister, second slits that extend across each end of the first linear slit formed by the primary cutting element, the primary and secondary cutting elements together forming flaps in the lid which are folded aside by said primary and secondary cutting elements, wherein the secondary cutting elements are configured so that they each form a substantially V-shaped slit in the blister lid as they enter the blister.

The secondary cutting elements are preferably configured so that the V-shaped slits point inwardly towards each other and each have their apex at the point of contact with the first linear slit cut by the primary cutting element.

According to another aspect of the invention, there is provided a blister piercing head for puncturing the lid of a blister containing a dose of medicament for inhalation by a user, the blister piercing head comprising a pair of separate, spaced cutting elements, each cutting element being configured to cut a substantially V-shaped slit in the lid of a blister when inserted therein so that the apex of one V-shaped slit points towards the apex of the other V-shaped slit, the cutting elements being configured to cause a region of the blister lid between the apex of the first and second V-shaped slits to burst during entry of the cutting elements into the blister.

In a preferred embodiment, each cutting element is substantially U-shaped with a cutting edge formed at the base of the U that bridges an airflow aperture into or out of a blister.

Preferably, the cutting elements are angled towards each other and the cutting edge may be formed at the end of a chamfered portion of the cutting element.

In a modified embodiment, the chamfered portion of one cutting element is larger than the chamfered portion of the other cutting element.

A bridging element may extend between the cutting elements to burst through the portion of the blister extending between the apex of each V-shaped slit.

Each cutting element preferably comprises a secondary cutting edge to initiate a slit in the blister lid in said region between the apex of said first and second V-shaped slits. According to another aspect of the invention, there is provided a blister piercing head for puncturing the lid of a blister containing a dose of medicament for inhalation by a user, the blister piercing head comprising a plurality of cutting elements extending in a radial direction from a central axis, each cutting element having a tip for initiating an incision in a lid of a blister spaced from the central axis and, a cutting edge extending in a radial direction from the tip of each cutting element to cut slits in the lid extending in a radial direction from the central axis to form flaps which are folded into the blister during insertion of the cutting elements in an axial direction into the blister through said lid.

In one embodiment, the cutting edge of each cutting element has a first portion extending radially inwardly from the tip to the central axis and a second portion extending radially outwardly away from the central axis.

Each cutting element is preferably a blade lying in a plane extending in a radial direction from the central axis and the cutting edge is formed along an edge of the blade.

Advantageously, the edge of the blade is chamfered to form the cutting edge.

Each blade may be provided with raised sections extending out of the plane of the blade to facilitate folding of the flaps into the blister.

In a preferred embodiment, the cutting elements upstand from a surface and extend over an airflow aperture which allows air to flow into, or out of, a blister.

Protruberances may upstand from the surface between the cutting elements to facilitate folding of the flaps into the blister.

In a preferred embodiment, there are four cutting elements extending from a central axis, each cutting element being substantially at right angles to its adjacent cutting element.

BRIEF DESCRIPTION OF DRAWINGS

Embodiments of the present invention will now be described, by way of example only, with reference to FIGS. 2 to 3 and 5 to 9 and 14 to 25 of the accompanying drawings, in which:

FIG. 3 is an enlarged view of FIG. 2D showing the path that agglomerates of medicament follow when they are entrained in an airflow and pass through an opening in the piercing element out of the blister;

FIG. 4 is an enlarged prior art view of FIG. 1D to show how agglomerates of medicament are prevented from passing through the opening in the piercing element and out of the blister by the lid flap which partially blocks the entrance to the opening;

FIG. 5 is a similar view to FIG. 3 showing how air flows into and out of the blister when pierced by a piercing element according to an embodiment of the present invention;

DETAILED DESCRIPTION

Figure 1:
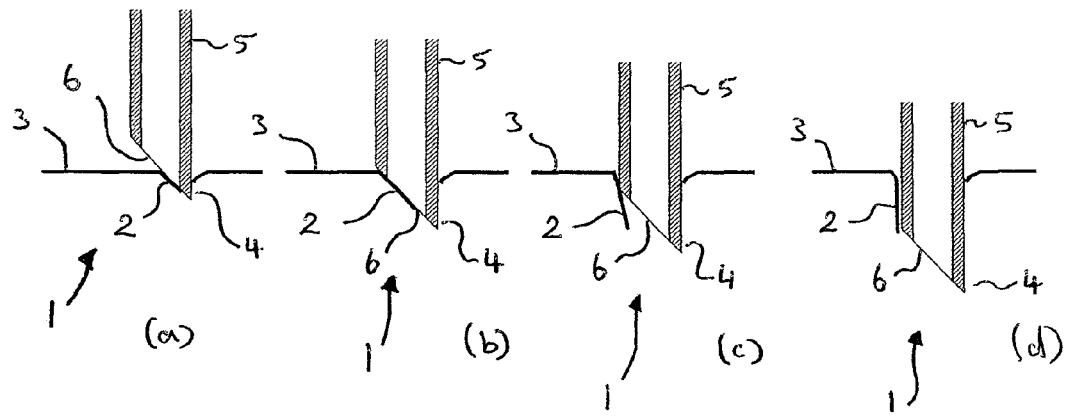
FIGS. 1A to 1D are prior art cross-sectional side views of a conventional piercing element as it pierces and enters a blister.
Figure 2:
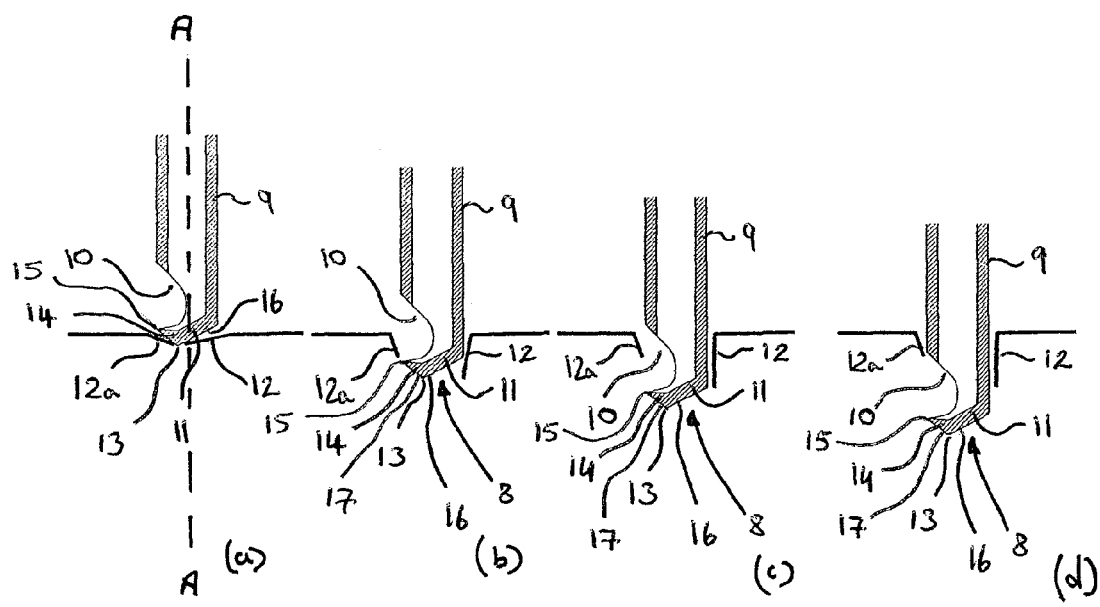
FIGS. 2A to 2D illustrate similar views to those shown in FIG. 1 using the piercing element according to an embodiment of the present invention.

Referring now to the drawings, the sequence of FIGS. 1A to 1D shows how a foil flap 2 is formed in the lid 3 of a blister 1 using a conventional piercing element 4 located at the end of a hollow tube 5 and from which it will be appreciated that the flap 2 will partially block the opening 6 at the distal end of the tube (see FIGS. 1(*a*) and 1(*b*)) unless the tube 5 is inserted relatively deeply into the blister 1 (see FIG. 1(*d*)). The partial blockage of the opening 6 by foil flap 2 is more clearly seen in the prior art drawing of FIG. 4 in which agglomerate 7 is prevented from passing into the tube 5 by the foil flap 2.

The sequence of FIGS. 2A to 2D is similar to that of FIG. 1, but the conventional piercing element 4 has been replaced with a piercing element 8 according to an embodiment of the present invention. The piercing element 7 is also in the form of a hollow tube 9 and has an opening 10 at its distal end. However, the distal end of the tube 9 has a piercing head or tooth 11 that continues in a longitudinal or axial direction beyond the opening 10 and extends in a radially inward direction across the end of the tube 9 or opening 10. The piercing head 11 forms the piercing element 8 that cuts a flap 12 in a lid 3 of a blister 1 and pushes it away from the opening 10 in the distal end of the tube 9 during insertion.

The piercing head 11 that continues beyond the end of the tube 9 preferably extends angularly away from but extends radially across the end of the tube and opening 10 by a distance greater than the radius of the tube 9 and tapers to a piercing tip or edge 13 located just offset from the longitudinal axis A (see FIG. 2A) of the tube 9. Although the piercing tip or edge 13 may be formed at the very end of the portion 11, in the embodiment shown in FIGS. 2, 3 and 5, it is formed proximal to said end of said portion 11. In this case, a part 14 of said portion 11 that extends beyond the piercing tip 13 is angled back towards the opening 10 in the tube 5 and tapers to a point 15. The edge 16 of portion 11 and edge 17 of part 14 form cutting surfaces. Edge 16 cuts flap 12 and edge 17 cuts flap 12*a* in the lid 3 of a blister 1. It will be appreciated that the piercing tip 13 is offset from the axis of the tube 9 so that the flaps 12, 12*a* are of unequal size, the larger flap 12 being formed on the side away from the opening 10 in the tube 9.

From a comparison of FIGS. 3 and 4, it will be appreciated that the drug moves in a more lateral direction substantially at right angles to the direction of insertion of the tube 9 into the blister 1 into the opening 10, as shown in FIG. 3, than in the prior art embodiment of FIG. 4. However, it will be appreciated that the portion 11 may not completely extend over the end of the tube 9 when viewed in an axial direction along the length of the tube 9 i.e. the portion 11 may be tapered or generally be thinner than the diameter of the tube 9 so that drug can pass into the tube 9 in an axial direction over the sides of the portion 11 as well as laterally, as illustrated in FIG. 3.

It will be appreciated that, in a more practical implementation, the piercing head 11 may upstand from the upper surface 34 of a piercing element such as that illustrated in FIG. 11 so as to extend over the apertures 37,38 formed therein, as will become apparent from the description of the various embodiments of the invention referred to in more detail below.

The tooth 11 may be generally "L"-shaped in side elevation and have a first leg upstanding from the periphery of the opening in a tube or piercing head and a second leg extending in a more lateral direction across and overhanging the end of the tube or aperture in the piercing element. The two legs of the tooth 11 need not be at right angles to each other and the join between the two of them may take the form of a smooth blended curve. Such a configuration will become more apparent from a consideration of the embodiment described with reference to FIGS. 19 to 25.

To enable the flow of air or gas through the blister 1 and out via the exit tube 9, an air inlet needs to be provided. This can be achieved by allowing the air to flow in through the annular gap 18 created between the outer diameter of the tube 9 and the lid 3, as shown in FIG. 5. FIG. 5 also shows how turbulence in the blister 1 assists in the drug entrainment and emptying process.

Figure 8:
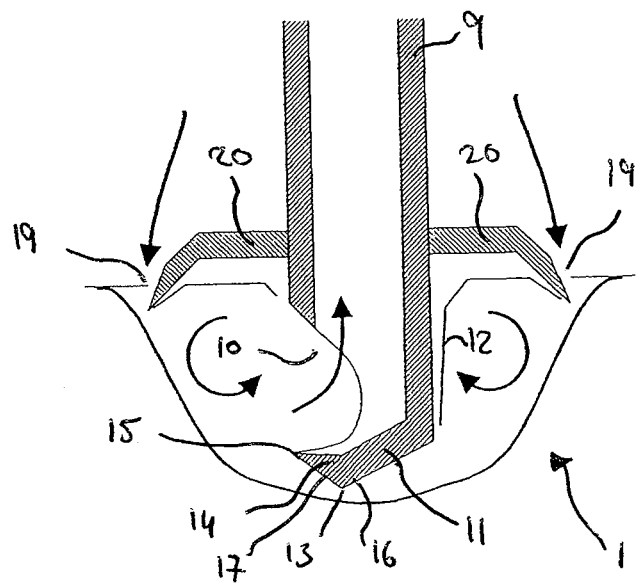
FIG. 8 shows a similar view to that of FIG. 5 but illustrates how additional air inlets can be created in the lid using a piercing "star"

An alternative embodiment for providing an airflow into the blister 1 is illustrated in FIG. 8 in which one or more additional air inlets 19 can be created in the lid 3 by the use of a secondary piercing element 20 in the form of additional pins, blades, tubes or the like, for example those described in the applicant's own earlier application PCT/GB2004/003940, published as WO 2005/025656 A1. A particularly preferred form of secondary piercing element 20 is in the form of a "star" that is carried on the tube 9 and pierces a series of openings 18 in the lid 3 of the blister 1 around the periphery of the tube 9, as shown in the cross-sectional view of FIG. 8.

Figure 9:
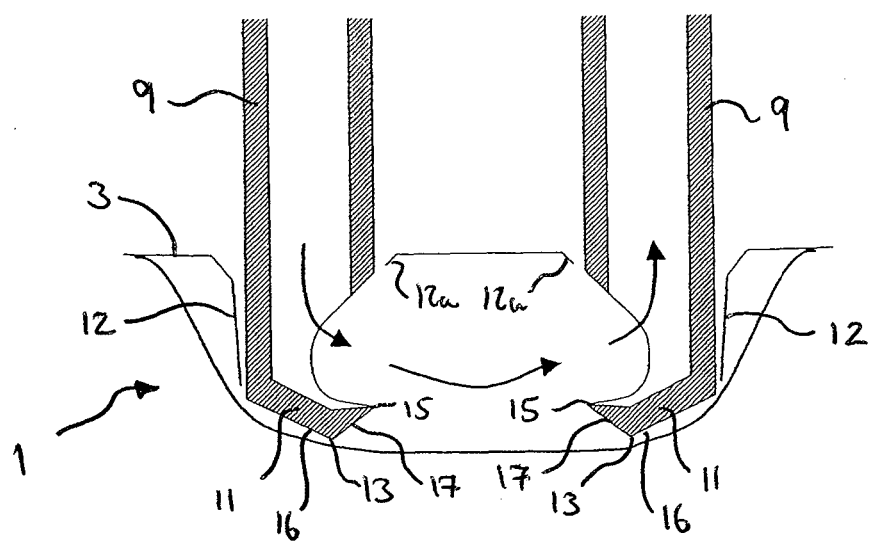
FIG. 9 illustrates another embodiment of the invention in which two piercing heads have been inserted into a blister, one tube forming an air inlet to the blister and the other forming an air/medicament outlet to the blister.

In an alternative embodiment, the secondary piercing element takes the form of a another outlet tube piercing element 21, as shown in FIG. 9, which is identical to the first piercing element. This is particularly useful if the blister 1 is an oval or approximately rectangular form rather than circular. The piercing elements can be arranged so that their openings face each other so as to enable a direct flow of air through the blister between the inlet and the outlet.

It will be appreciated that the piercing element of the present invention may take different forms to produce a different form to the cut foil flap. However, the overall intention is that the piercing head pushes the cut foil flap 12 away from the opening 10 to prevent it from interfering with the flow of medicament and air out of the blister 1.

Figure 6:
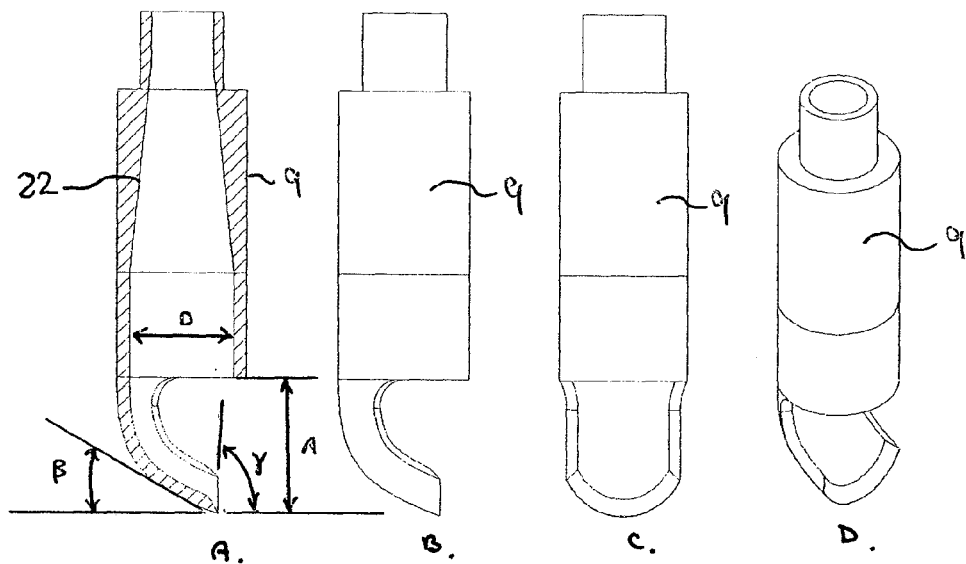
FIG. 6A to 6D shows a cross-sectional side view, a side view, a front view and a perspective view, respectively, of an alternative piercing element according to the present invention.
Figure 7:
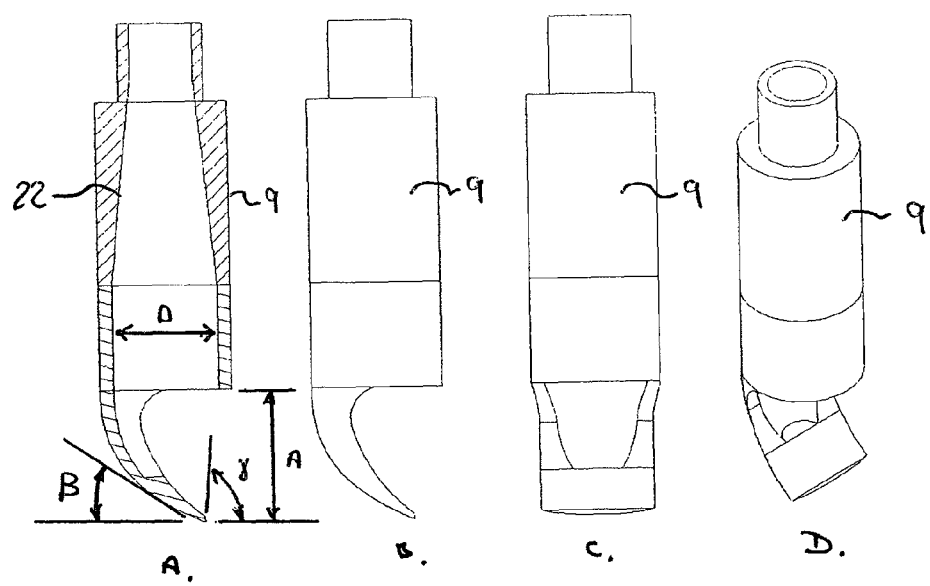
FIG. 7A to 7D shows a cross-sectional side view, a side view, a front view and a perspective view, respectively, of yet another alternative piercing element according to the present invention.

Two possible alternative embodiments of piercing element according to the invention are illustrated in FIGS. 6 and 7. It can also be seen that, from FIGS. 6A and 7A, both of these designs feature a tapered outlet tube 22 for connection to an aerosolising nozzle.

The dimensions A and D in FIGS. 6A and 7A influence the ability of the piercing element to entrain larger agglomerates of powder. Preferably A is greater than 1 mm. More preferably A is greater than 2 mm and less than 5 mm. In the embodiments of FIGS. 6 and 7, A is 2.5 mm. Preferably D is greater than 1 mm. More preferably D is greater than 1.5 mm and less than 5 mm. In the embodiments of FIGS. 6 and 7, A is 2 mm.

The angles β and γ of the two tangents of the tip of the cutting element relative to the surface of the foil are important in controlling the nature of the piercing. If the angle β is too small the piercing head will tend to burst through the foil in a potentially uncontrolled and therefore inconsistent manner. It is preferable for β to be sufficiently large to make a clean cut rather than a burst through the foil. Preferably the angle is greater then 5° and less than 60°. More preferably the angle is greater then 10° and less than 30°. In the embodiments of FIGS. 6 and 7 the angle is substantially 20°.

Similarly, the angle γ needs to be large enough to provide a sharp point on the tip of the piercing head. Preferably the angle is greater then 30°. More preferably the angle is greater then 60° and less than 90°. In the embodiments of FIGS. 6 and 7 the angle is substantially 90°. It will be appreciated that no further advantage is gained in the quality of the piercing cut from having an angle γ of greater than 90°. However, the embodiment of FIG. 6 includes a chamfer on the inside of the piercing edge which advantageously provides a lead-in to facilitate the flow of powder into the piercing element.

In a further embodiment (not illustrated), the tip of the piercer may be provided with an "egg tooth" feature to facilitate the start of the cut. In this case the included angle of the egg tooth is critical in facilitating a clean cut. Preferably the included angle is less than 100° and more preferably less than 60°.

The piercing element can be made from a suitable rigid material such as metal or plastic. If made of metal the tube and cutting feature can be machined or spark eroded. Plastic materials may be either machined or injection moulded. To simplify the construction the tube may be made from more than one part and subsequently assembled.

In the embodiment of FIG. 9, two tubes 9, each with a piercing element 8, have been inserted into a blister 1. The tubes 9 are oriented so that the openings 10 at the distal end of each tube 9 face each other so that air flows into the blister 1 via one tube 9 and out of the blister 1, together with the entrained drug, through the other tube 9. However, it will be appreciated that the tubes 9 may be positioned so that the openings 10 face in opposite directions to each other to create more swirl in the airflow as it passes through the blister with the aim of scouring the blister more thoroughly to prevent drug from becoming trapped behind the flaps cut by the piercing element 8. Such an arrangement will be explained in more detail with reference to FIGS. 18 to 25.

The present invention also provides a modified embodiment of the 'H' shaped piercing element shown in FIG. 10A, previously described with reference to FIGS. 8A and 8B of the Applicant's co-pending application no PCT/GB2004/004416. The shape of the piercing head is important as the openings that are formed in the lid of the blister 1 must be of a sufficient cross-sectional area to promote the free-flow of air through the blister 1 and to ensure that all, or substantially all, the dose is entrained and carried out of the blister 1 in the airflow.

Figure 10A:
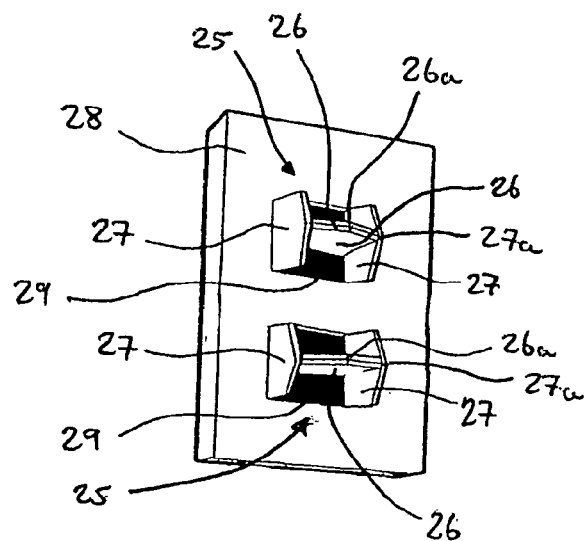
FIG. 10A illustrates a conventional form of piercing element having two piercing heads and, FIG. 10B illustrates a small portion of a strip of blisters to illustrate the type of cut made by the conventional form of piercing element shown in FIG. 10A.

Referring now to the prior art drawing of FIG. 10A, each piercing head 25 comprises a primary cutting tooth 26 and a pair of secondary cutting teeth 27 extending laterally across each end of the primary cutting tooth 26 so that the secondary cutting teeth 27 are each perpendicular to the primary cutting tooth 26. Each of the primary and secondary cutting teeth 26,27 taper towards a sharp point 26a, 27a and the height of the mid-point of the secondary teeth 27 is such that the points of the secondary teeth 27 are at the same height as the edges of the primary tooth 26. The edges of all the teeth may be sharpened to help them to cut the lidding foil 3 of the blister 1. As the pointed tip 26a of the primary cutting tooth 26 is above the pointed tip 27a of each of the secondary cutting teeth 27, the primary cutting tooth 26 slits or at least initiates a slit in the blister lid 3 before either of the secondary cutting teeth 27 begin to cut second linear slits in the blister lid 1. The supporting plate 28 from which the primary and secondary cutting teeth 26,27 upstand, has holes 29 cut into it beneath the primary and secondary piercing teeth 26, 27 to allow a free flow of air therethrough.

Figure 10B:
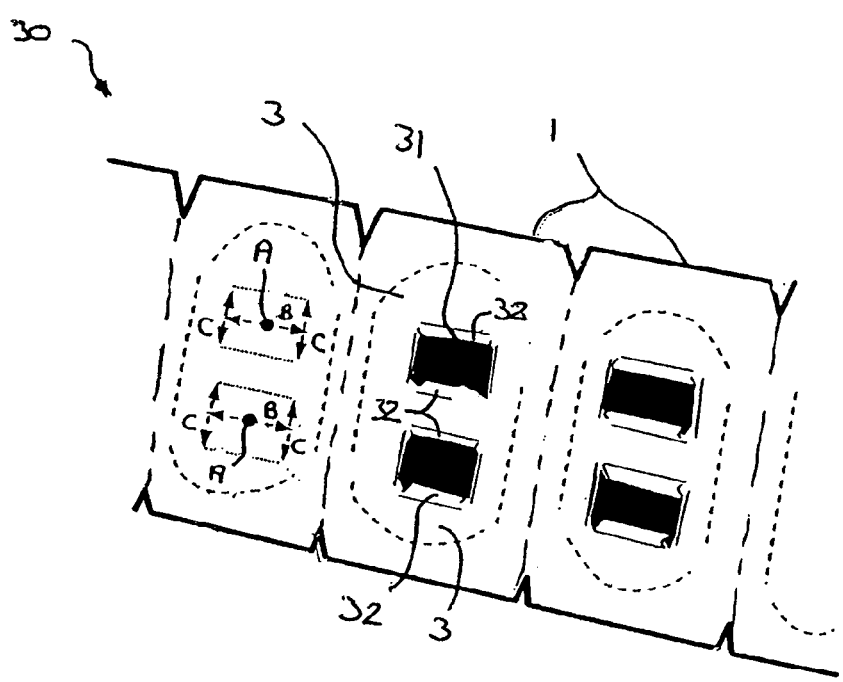

FIG. 10B shows a short section of strip 30 of blisters to show the shape and size of the openings 31 that each of the piercing heads 25, described with reference to FIG. 10A, cut in the lid 3 of a blister 1. The primary cutting teeth 26 penetrate the lid 3 (point A) and, as they enter the blister 1, two linear cuts or slits are made by each of them, as indicated by arrows "B". As the piercing head 25 further enters the blister 1, the secondary cutting teeth 27 penetrate the blister 1 and further linear cuts are made at each end of the linear cuts "B" perpendicular to the first linear cut "B" formed by the primary piercing element 26, as indicated by arrows "C". These cuts have the effect of creating flaps 32 that are folded back into the blister as the piercing head 25 enters further into it. The piercing heads 25 are capable of forming openings 31 that extend to over 30 to 50% of the surface area of the lid 3 of a blister 1.

A practical implementation of the conventional piercing element described above is shown in FIG. 11 and comprises a main body portion 33 having an upper surface 34 that lies flush against the upper surface of a lid 3 of a pierced blister 1 when the piercing head has fully entered a blister 1. The piercing heads comprises one piercing tooth 35 upstanding from the upper surface 34 and another piercing tooth 36 upstanding from a relieved or recessed region 34a of the upper surface 34. Apertures 37,38 are formed in the upper surface 34 and recessed region 34 beneath teeth 35,36, respectively. Each piercing tooth 35, 36 comprises a primary cutting element 40 and secondary cutting elements 41 extending across the end of the primary cutting element 40, as described with reference to FIGS. 10A and 10B. Further details and precise dimensions of the angles of the cutting surfaces are described in more detail in the Applicants co-pending international PCT patent application no. GB04/004416, with specific reference to FIGS. 27A and 27B.

Figure 12:
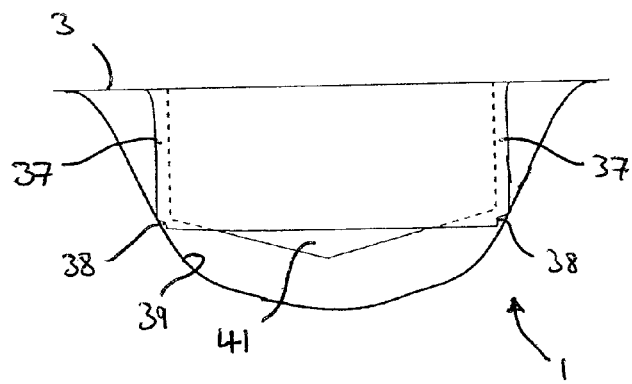
FIG. 12 is a side sectional view showing the end face of a conventional secondary cutting element and flap formed thereby.

A problem with the conventional piercing heads 35,36 described above, is that the secondary cutting elements 41 cut generally rectangular shaped flaps 37 (see end view of FIG. 12 showing an end face of one secondary cutting element 41) whose corners 38 touch or are very close to the blister wall 39 when folded inwardly by the secondary cutting elements 41. This reduces the free-flow of air and hence the movement of powder in the blister 1. The end view of FIG. 12 is also repeated in FIG. 13a, together with a top plan view when inserted through a lid 3 (FIG. 13b), side view when inserted through a lid of a blister (FIG. 13c) and top plan view before insertion through a blister (FIG. 13d) which clearly shows the H-Shape of the piercing head.

Figure 13:
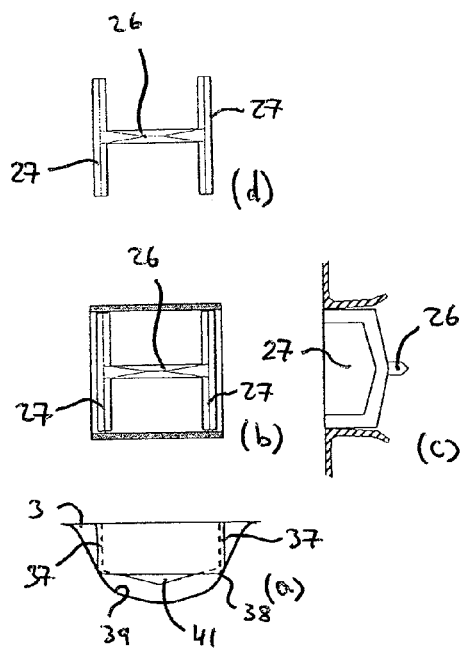
FIGS. 13A to 13D show various views of a conventional piercing head.

It is therefore desirable for the flaps formed by the secondary cutting elements 41 to be shaped so that the distance between the corner 38 of the flap 37 and the inner wall 39 of the blister 1 is larger and most preferably, so that the edge of the flap 37 generally corresponds in shape to the curvature of the blister wall 39. This can generally be achieved by cutting the flaps 37 so that they are trapezoidal or triangular in shape, rather than rectangular, so that their edges converge inwardly and so more closely follow the form of the blister wall, as shown, for example, in FIG. 14a which illustrates the same cross-section through a blister showing the end face of the secondary piercing tooth as shown in FIG. 12 and FIG. 13a but in which the tooth has a modified shape to form flaps 45 having angled or converging edges 46. FIGS. 14b and 14c show a plan view and side sectional view, respectively, of the primary and secondary cutting teeth when inserted through a lid 3 of a blister 1, according to the modified embodiment of the invention and FIG. 14d shows a plan view prior to insertion of a conventional piercing head into a blister 1.

As can be most clearly seen from FIG. 14d, to make the flaps trapezoidal or triangular in shape and give increased distance between the flap and the blister wall, the secondary teeth are not single flat plates extending across each end of the primary cutting element, as with the conventional "H"-shape piercer. Instead, each secondary tooth comprises a "V" or chevron shaped element 48 having its apex 49 at the point where it joins the primary cutting element 50. Each chevron shaped element is configured to point inwardly towards the primary cutting element 50. This arrangement initially cuts substantially V-shaped slits in the blister lid and subsequently forms trapezoidal or triangular shaped flaps 51 in the blister lid 3 as the piercing head is inserted into the blister 1, to give improved clearance between the flap 51 and the blister wall 39 and provide a free flow of air into the blister 1 to reduce the interference to the flow of air caused by the flaps cut by conventional secondary teeth 27,41.

It will be appreciated that the angle of the secondary cutting teeth 48 with respect to the primary cutting tooth 50 may be varied and that the length of the primary cutting tooth 50 may be varied to the extent that it is so short that the apex 49 of each of the secondary cutting teeth 48 are practically in contact with each other and the primary and secondary cutting teeth 48,50 together form an "X" shape in plan view. Preferably the angle α between a secondary cutting tooth and the primary cutting tooth viewed in plan is between 100° and 135°. In the embodiment of FIG. 15, the angle α is substantially 130°.

Figure 11:
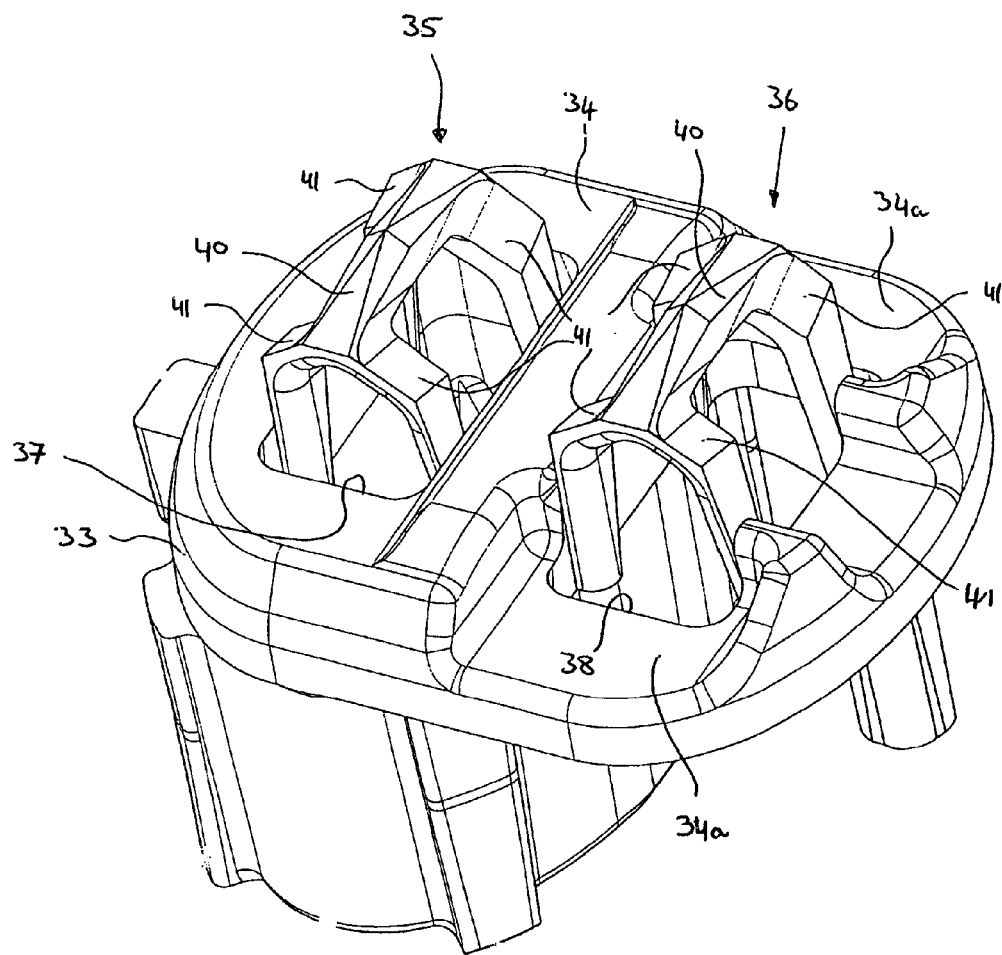
FIG. 11 illustrates a perspective view of a conventional practical implementation of a piercing element of FIG. 10A.

A practical implementation of the modified piercing element described above is shown in FIG. 15, and is generally similar to the practical implementation described above with reference to the conventional piercing element shown in FIGS. 10A, 10B and FIG. 11, except that the secondary cutting teeth 48 are modified, as described above, so that they initially form generally V-shaped slits in the blister lid 3 and triangular shaped flaps which do not contact the interior of the blister wall.

Figure 14:
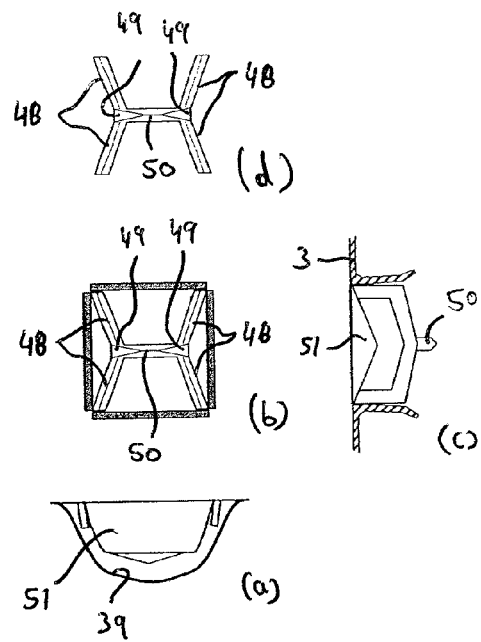
FIG. 14A to 14D show various views of a modified piercing head according to the invention.
FIG. 14E shows a top plan view of a blister lid to illustrate the flap shape that is cut using a piercing head as shown in FIG. 14A to 14D.
Figure 14E:
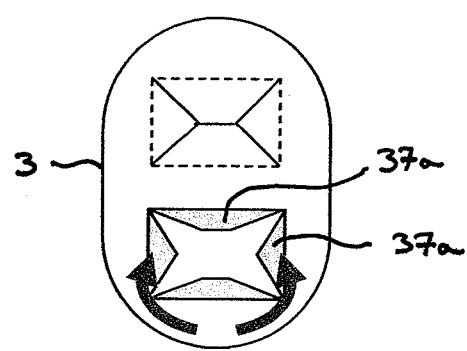
Figure 15A:
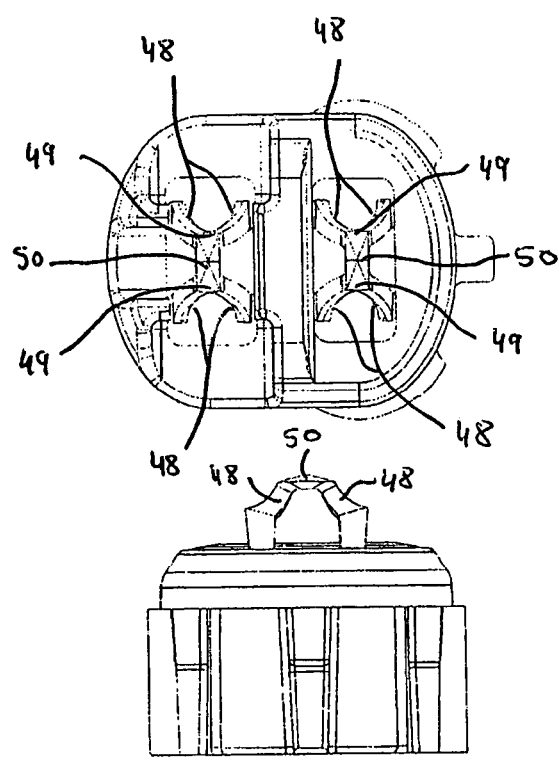
FIG. 15A to 15D shows an end, top plan, side and perspective view, respectively, of a practical implementation of a piercing element according to an embodiment of the invention.
Figure 15C:
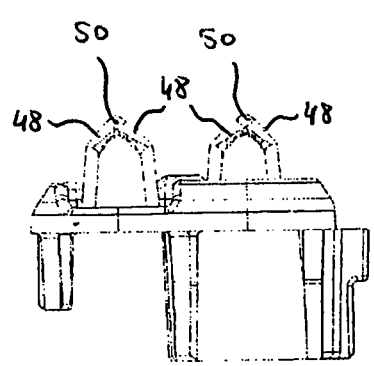
Figure 15B:
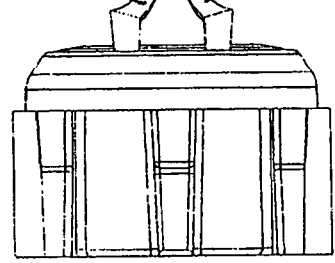
Figure 15D:
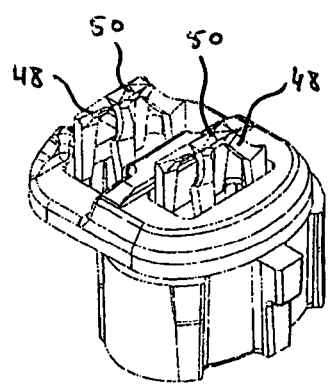

It will be appreciated that the above described embodiment opens four substantially triangular or trapezoidal shaped flaps 37a, as shown in FIG. 14E, as opposed to the two rectangular flaps. The triangular flaps 37a at each end of the blister 1 are not so close to the blister base when open and so allow a greater airflow behind them which assists in the evacuation of powder from the blister 1. The piercing element described with reference to FIGS. 14 and 15 has become known as the "envelope" type piercer, in view of the slits cut in the blister lid which resemble that of an envelope, as will be apparent from FIG. 14E.

Figure 16:
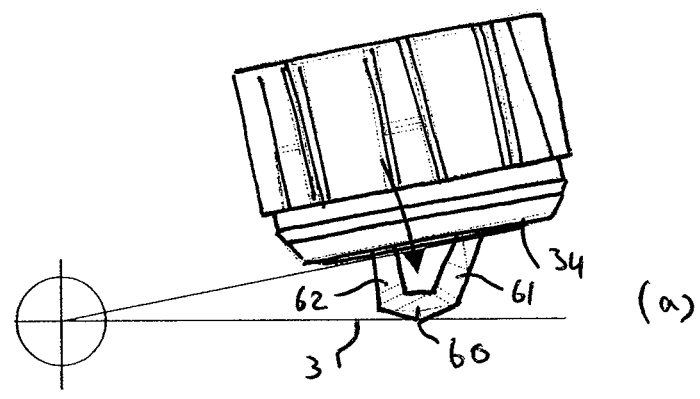
FIGS. 16A and 16B illustrate a piercing element according to the present invention to show how the angle of the piercing heads may be skewed when they follow an arcuate path into a blister lid.
Figure 16:
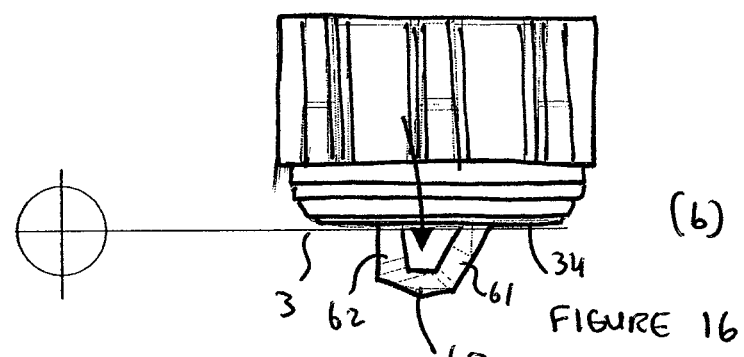
Figure 17:
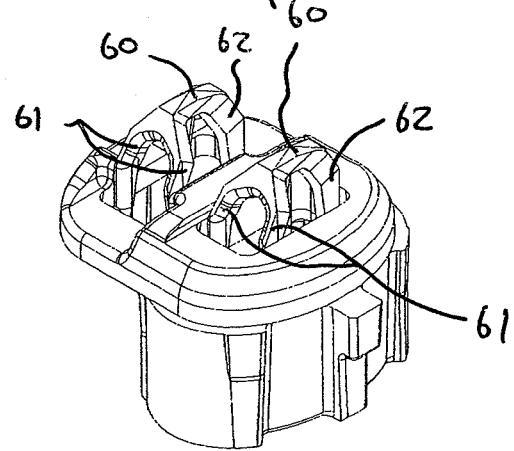
FIG. 17 illustrates a perspective view of the piercing element shown in FIGS. 16A and 16B.
Figure 18:
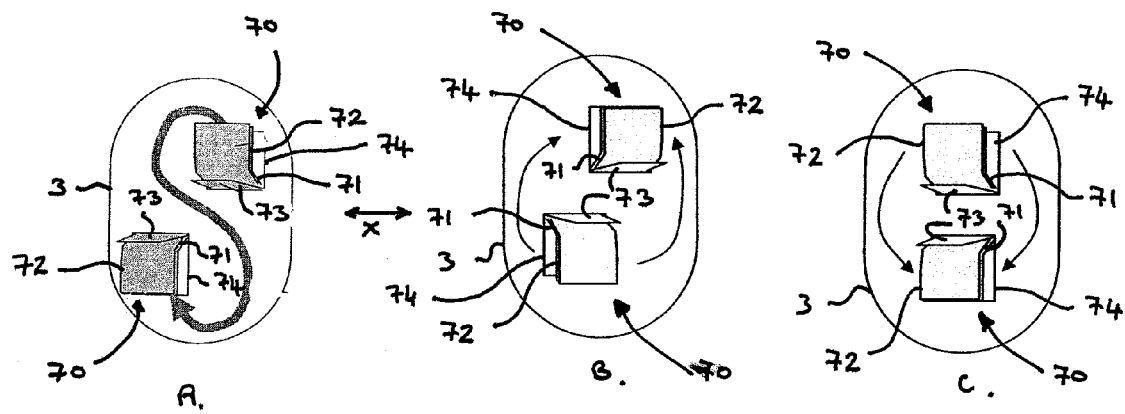
FIG. 18A to 18C show three alternatives of a slightly perspective view of the underside of a blister lid following puncturing by two blister piercing heads in different relative positions to each other.
Figure 19:
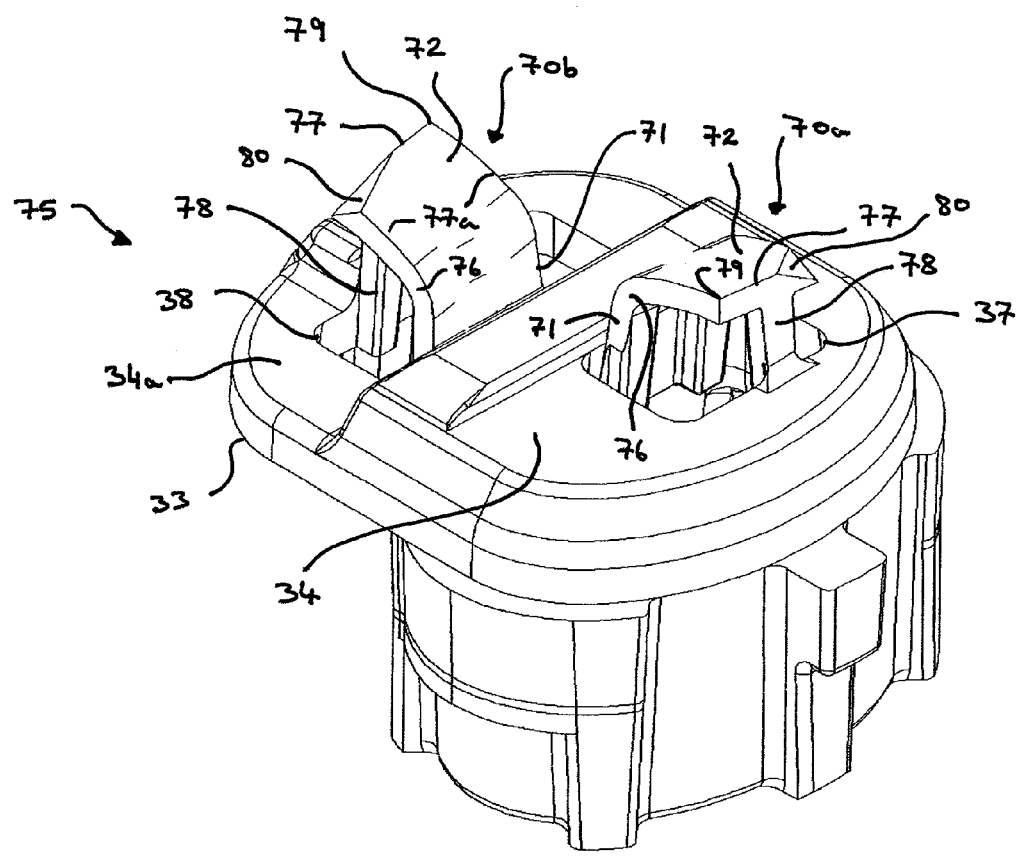
FIG. 19 shows a perspective view of a piercing element forming a practical implementation of the piercing arrangement shown in FIG. 18.
Figure 20:
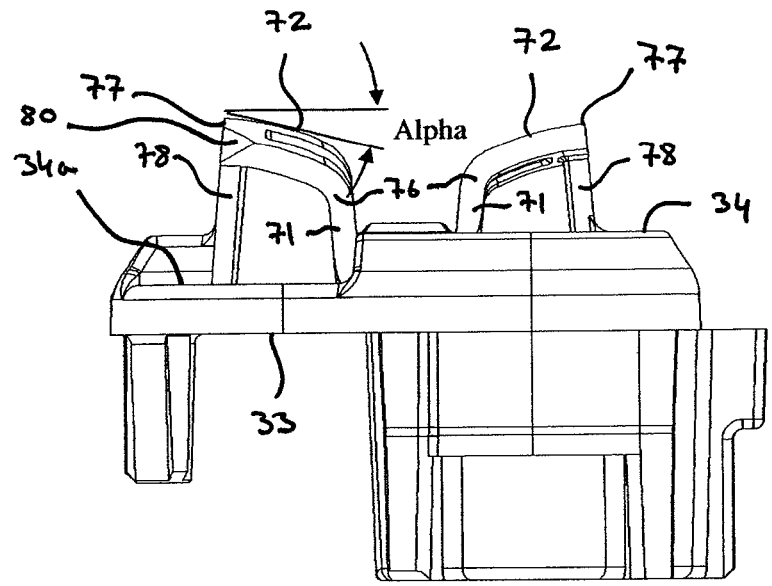
FIG. 20 shows a side elevation of the piercing element illustrated in FIG. 19.
Figure 21:
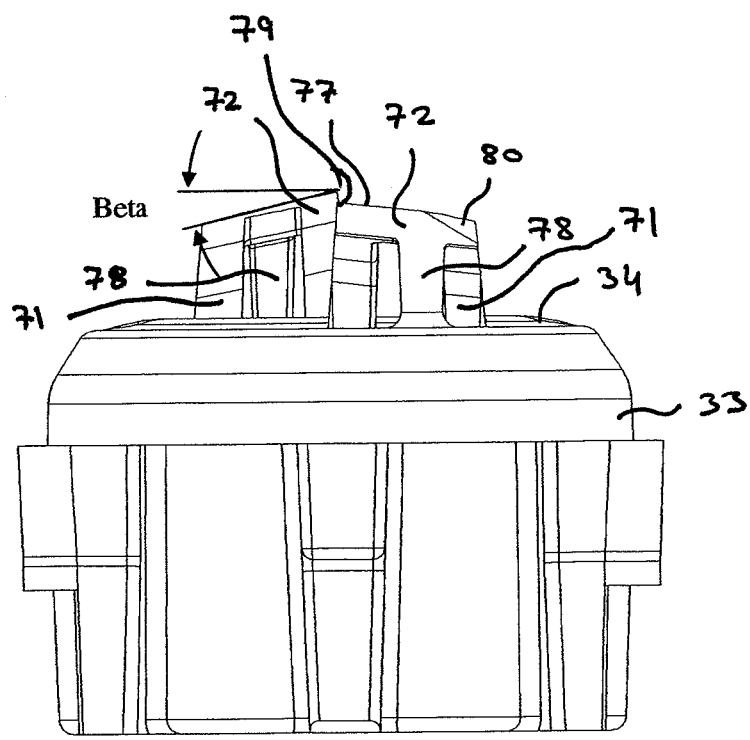
FIG. 21 shows an end elevation of the piercing element illustrated in FIGS. 19 and 20.
Figure 22:
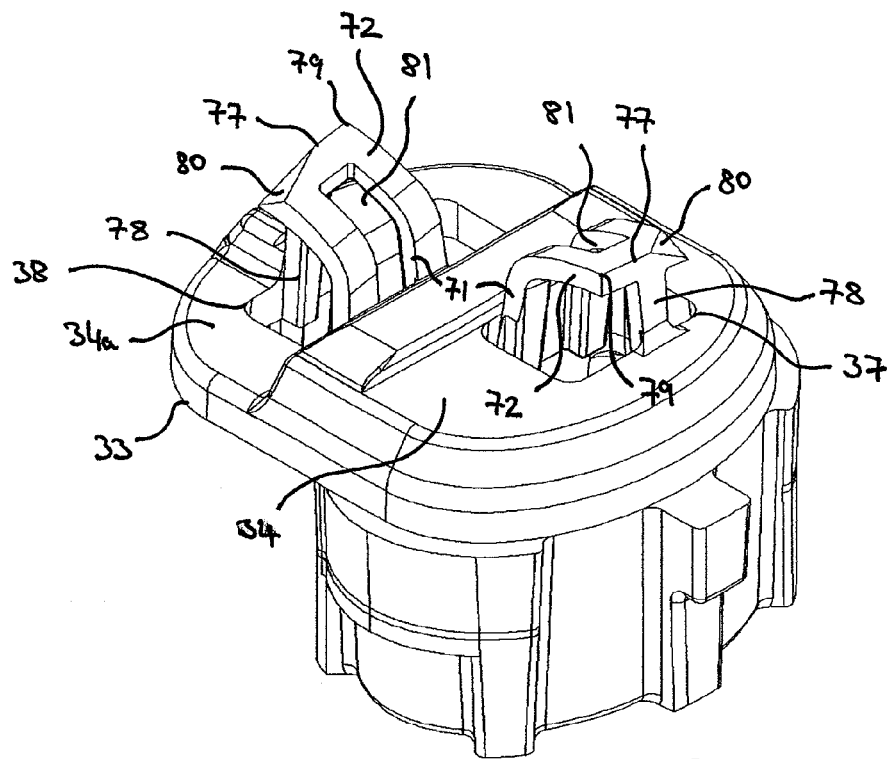
FIG. 22 shows a perspective view of another modified embodiment of piercing element, similar to that illustrated in FIG. 19.
Figure 23:
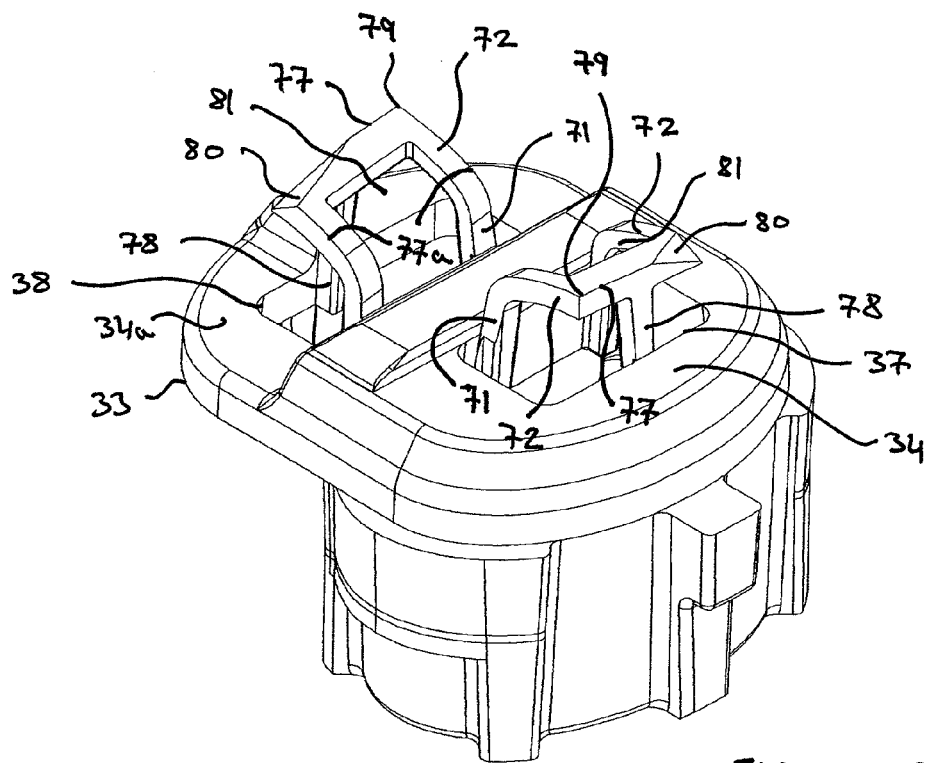
FIG. 23 shows a perspective view of yet another modified embodiment of piercing element, similar to that illustrated in FIGS. 19 and 22.
Figure 24:
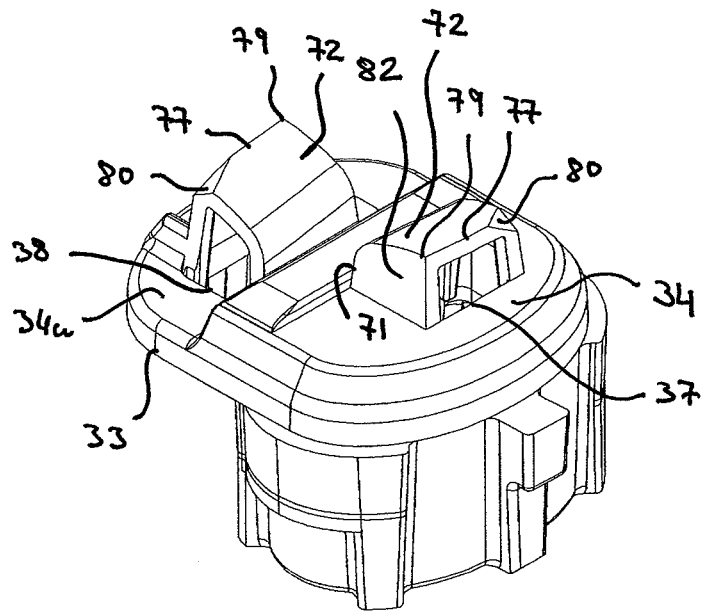
FIG. 24 shows a perspective view of yet another modified embodiment of piercing element, similar to that illustrated in FIGS. 19, 22 and 23.
Figure 25:
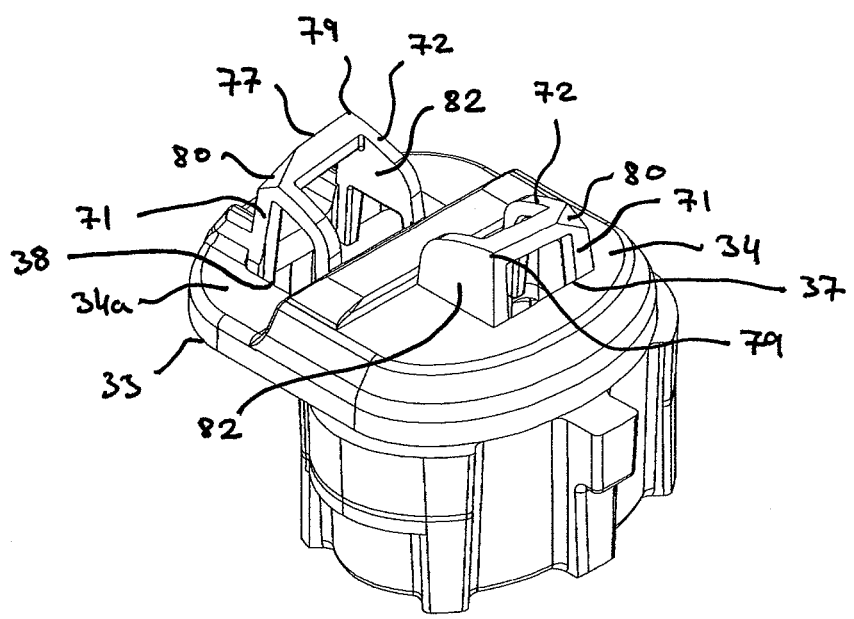
FIG. 25 shows a perspective view of yet another modified embodiment of piercing element, similar to that illustrated in FIGS. 19, 22, 23 and 24.

In another embodiment of the conventional practical implementation of the piercing element described above and shown in FIGS. 10A, 10B and 11, the piercing heads can be modified to take into account the way in which the element is inserted into the blister lid. For example, an inhaler which includes one or more piercing heads to enable access to a blister will typically incorporate a mechanism to control the position of the piercing heads and the way in which the heads are inserted. The mechanism may, for example, control the piercing head such that it enters the blister following a substantially linear direction perpendicular to the plane of the blister lid. However, it is more likely that the piercing element will be located on a pivoting actuating member, such that the element moves in a an arc as the piercing heads pierces a blister. In this case it is advantageous to modify the piercing heads to ensure that the foil flaps are formed correctly and so that initial piercing of the foil lid is carried out as intended by the 'point' of the primary tooth. This is achieved by forming the primary cutting tooth 60 at an angle with respect to the upper surface 34,34a of the piercing element from which the piercing heads upstand so as to compensate for the angle between the upper surface of the piercing element and the blister lid 1 at the point of contact of the tip of the primary cutting tooth with the blister lid 3, as shown in FIGS. 16 and 17. This can be achieved by making one of the secondary cutting elements 61 protrude further from the upper surface 34 of the piercing head than the other secondary cutting tooth 62 so that the primary cutting element 60, which extends from the top of one secondary cutting tooth 61 to the top of the other secondary cutting tooth 62, is angled with respect to the upper surface 34 of the piercing element.

A further embodiment, referred to by the Applicant's as a "double-beak" piercer, will now be described with reference to FIGS. 18 to 25. It will be apparent that this embodiment is similar to that shown in FIG. 9, except that the piercing heads or teeth are positioned in a "back-to-back" relationship so that the openings face away from each other rather than towards each other, as shown in FIG. 9.

With small excipient particles (typically in the range 20-100 μm in diameter), powder may be readily evacuated from a blister using a piercing element with conventional piercing heads. However, some formulations contain either large excipient particles with particle sizes between 100 and 500 μm or agglomerations of smaller particles in a similar size range. A conventional piercing head is less able to thoroughly evacuate these powders as the flow path between the inlet and outlet is not open sufficiently creating "dead" areas where powder can become trapped. The present embodiment overcomes this limitation by creating a larger opening unencumbered by a flap, as the flap is behind the piercing head, and by directing the airflow so that it scours the area behind the flaps and near the ends of the blister.

Referring first to FIG. 18A to 18C, there is shown the underside of a blister lid 3 into which two piercing heads 70, forming part of the same piercing element, have been inserted. Each piercing head 70 is in the form of a blade like element comprising a first leg portion 71 which generally extends in the direction of insertion, or which is only angled away from the direction of insertion to a small extent as shown and, a second leg portion 72 which extends in a more lateral direction from the end of the first leg portion 71 and overhangs apertures 74 formed in the blister lid 3 by each of the piercing heads 70. As the second leg portion 72 of each piercing head 70 punctures the lid 3 to form apertures 74, they create flaps 73 which are folded down into the blister and lie against the first leg portion 71 so as not to block airflow through the apertures 74 in the lid 3.

Although the piercing heads 70 are in a back-to-back relationship, i.e. the back of each first leg portion 71 of each piercing head 70 face toward each other, as does the interior surface of the foil flaps 73, they need not be in lateral alignment, as shown in FIG. 18C. On the contrary, the piercing heads 70 may be offset from each other, as shown in FIG. 18A or 18B and in the direction indicated by "X", to encourage greater swirl of the air flow passing through the blister 1. In FIG. 18C, the piercing heads 70 are in complete alignment whereas in FIG. 18B, the piercing heads 70 partially overlap in the "X" direction. In FIG. 18A, there is no overlap between the piercing heads at all, thereby creating a more "S" shaped flow path between the openings 74.

The following table shows evacuation data for several grades of lactose used for inhalation. The conventional inhalation lactose (espitose SV003, DMV International Pharma, The Netherlands), is evacuated repeatably as indicated by the residual standard deviation (RSD) by both the conventional piercer design and the piercing head of the present embodiment. The larger Capsulac grade is not evacuated repeatedly by conventionals. However, with the piercing head of the present embodiment, evacuation repeatability as indicated by the residual standard deviation (RSD) is significantly improved.

Comparison of performance of different lactose grades using a conventional piercing with the double beak piercer.

| Lactose | Information | Typical particle size (um) | Mean ex Blister (%) | RSD % ex-blister | Range ex Blister (%) | Piercing head |
|---|---|---|---|---|---|---|
| Respitose SV003 | sieved lactose, inhalation grade | 60 | 98.5 | 2.7 | 94-104 | Prior art FIG. 11 |
| Respitose ML001 | milled lactose, inhalation grade | 45 | 97.6 | 3.4 | 90-102 | Embodiment of FIG. 18 |
| Capsulac 212 - 355 μm | large fissured lactose | 250 | 89.6 | 20.4 | 37-112 | Prior art FIG. 11 |
| Capsulac 212 - 355 μm | large fissured lactose | 250 | 92.6 | 3.7 | 84-98 | Embodiment of FIG. 18 |

13 mg blister fill; 55 L/min flow rate. (Capsulac 60, Meggle AG, Germany, sieved to obtain the fraction which passes through a 355 um sieve is retained by a 212 um sieve)

FIG. 19 shows a practical implementation of the piercing heads shown in FIG. 18 comprising a piercing element 75 from which the piercing heads 70 both upstand. The piercing element 75 has a similar construction to the piercing element illustrated in FIG. 11, except that the piercing heads have a different configuration. As described with reference to FIG. 11, the piercing element may comprise a main body portion 33 having an upper surface 34 that lies flush against the upper surface of a lid 3 of a punctured blister 1 when the piercing head 70 has fully entered the blister 1. The piercing heads 70 comprise one piercing tooth 70*a* upstanding from the upper surface 34 and another piercing tooth 70*b* upstanding from a relieved or recessed region 34*a* of the upper surface 34. Apertures 37,38 are formed in the upper surface 34 and recessed region 34*a* beneath teeth 70*a*, 70*b*, respectively. Aperture 38 forms an airflow inlet into the blister whilst aperture 37 forms an airflow/drug outlet from the blister.

As described with reference to FIG. 18, each piercing tooth 70 has a first leg portion 71 upstanding from the surface 34,34*a* and, a second leg portion 72 extending laterally from the end of the first leg portion 73 so as to extend, at least partially, over the apertures 37,38. It can be seen that the first and second leg portions 71,72 blend smoothly into each other in the region of a curve 76 between them. The distal end of the second leg portion 72 has a primary cutting edge 77 which makes initial contact with the lid 3 of a blister 1 during insertion and cuts a first incision in the lid 3 to form a flap 73 which is subsequently folded away by the piercing head 70 as it moves further through the lid 3 into the blister 1. Secondary cutting edges 77*a* extend along each side of the piercing head 70 from the primary cutting edge 77 to the surface 34,34*a* so as to cut secondary slits in the blister lid substantially at right angles to the slit formed by the primary cutting element 77 and thereby form a substantially rectangular flap of foil attached to the remainder of the blister lid 3 along only one edge which is pushed inside the blister 1 by the piercing head 70 as it continues to enter the blister 1.

A support leg 78 extends from the distal end of the second leg portion 72 towards the surface 34,34*a* close to the aperture 37,38, although this support leg 78 is not essential and can be omitted.

From a consideration of the side and end elevations of FIGS. 20 and 21, it will be appreciated that the second leg portion 72 is angled away from the horizontal or the plane of the blister lid 3 in two directions so that only a tip 79 of the cutting edge 77 makes initial contact and incision into the blister lid 3. The rest of the second leg portion 72 falls away from the tip 79 towards the first leg portion 71 and the upper surface 34,34*a* of the piercing element. The tip 79 is the highest point of the piercing head 70 and is furthest from the surface 34,34*a*. The piercing heads 70 are configured so that the tip 79 is towards the centre of the blister 1 as the blister is deeper at this point and so is able to accommodate the piercing head without coming too close to the blister wall, as shown in FIG. 21.

The inventors have found that there must be a sufficient cutting angle to the foil to ensure accurate and consistent piercing. These angles, defined by "alpha" and "beta" in FIGS. 20 and 21, and they are typically in the range 5 to 45 degrees. Larger angles are less desirable as they tend to constrict the airflow through the piercing element.

The cutting edge 77 may be shortened by removing a section 80 of the second leg portion 72 at the lower end of the cutting edge remote from the cutting tip 79, as shown in FIGS. 19 to 21.

The piercing heads 70 described with reference to FIG. 19 are of the "closed" type, i.e. the first and second leg portions 72,73 are solid unbroken walls. However, in a modified embodiment, the piercing heads can be of the "open" type, in which case a central region 81 of the first and second leg portions 72,73 is cut away to form an opening therethrough, as shown in FIGS. 21-23 and 25. Although the closed version gives more control over the direction of the air entering the blister, the open version allows for an increased airflow. It will be appreciated that the opening 81 may be of any size and can be such that the leg portions 71,72 are substantially in the form of a wire frame as opposed to a blade like element, as is suggested by the modification shown in FIG. 23 in which the piercing heads create a much larger opening in the blister lid 3.

To provide further control over the airflow, one or more sidewalls 82 may be provided to partially enclose the piercing head, as shown in FIGS. 24 and 25.

Two further developments of the "envelope" type piercing element described with reference to FIGS. 14 and 15 will now be described.

Figure 26:
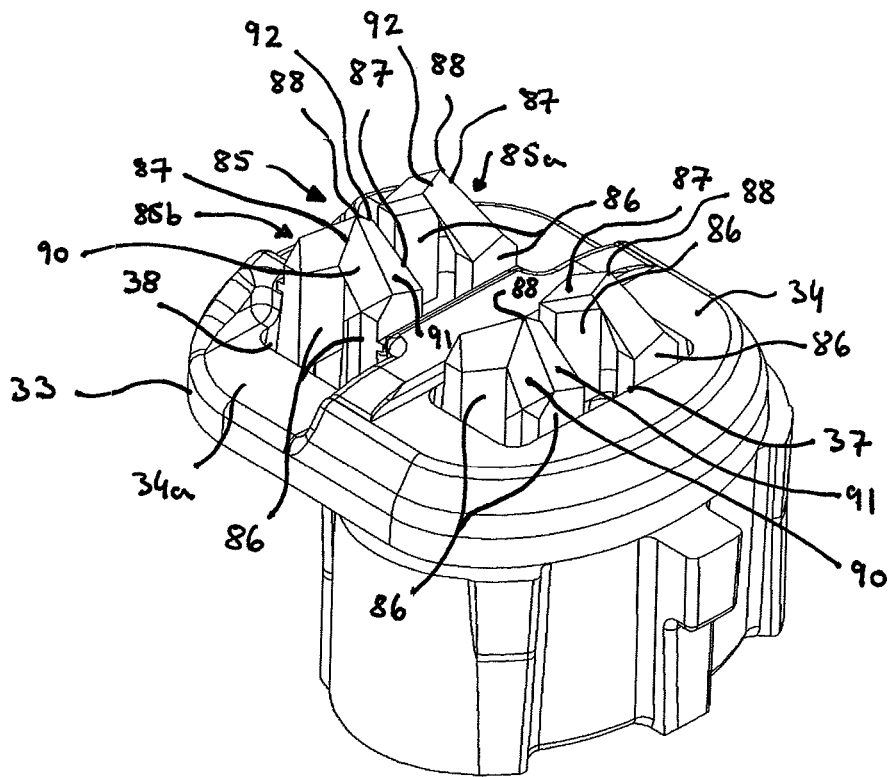
FIG. 26 shows a perspective view of another embodiment of piercing element according to the present invention.

FIG. 26 is a perspective view of a piercing element which is similar to the piercing element described with reference to FIGS. 11, 15 and 19 to 25, with the exception that the piercing heads have a different or "double-U" shaped configuration to substantially overcome or alleviate the problems referred to below.

When the piercing element is injection moulded polymer, the sharpness of the cutting edges is determined by the smallest radius that can be obtained from the injection moulding process for a given material. The smallest radius that can be obtained with a material such as ABS on the cutting edges is typically 50 microns minimum which is relatively blunt compared with, for example, the edge achievable on a metal blade. A conventional polymer such as ABS is also considerably softer than a metal which also affects the cutting quality. This means that, under certain conditions of piercing and particularly with weaker lidding foil, a moulded shallow envelope piercer may fail to make the desired cuts in the foil. In the worst case, the lid of the blister may collapse rather than form two clear well defined openings. One reason for this is that when making a cut from nearer the centre of the blister lid towards the edges of the blister, the foil being cut is less well supported than, for example, when making a cut from the outside towards the centre of the blister lid.

The present embodiment is designed to overcome the aforementioned problems and produce a similar cut pattern to the shallow envelope type piercing element described with reference to FIGS. 14 and 15, but in a more consistent and controlled manner.

As can be seen in FIG. 26, each piercing head 85 comprises a pair of generally "U" shaped elements 85a, 85b. Each U-shaped element comprises a pair of uprights 86 upstanding from the surface 34,34a of the piercing element on either side of an airflow aperture 37,38. A bridging portion 87 extends from the top of each facing pair of uprights 86 at an upward angle and towards each other so that they meet at an apex 88 at a mid-point between the uprights 86.

In addition to being angled in an upward direction away from the apertures 37,38 and the surface 34,34a of the piercing element, the bridging portions of each U-shaped element 85a,85b associated with the same aperture 37,38 are angled inwardly or lean towards each other in the same way in which the secondary cutting elements 48 of the embodiment of FIGS. 14 and 15 are angled inwardly and each form a V-shape pointing towards the primary cutting element 50.

The bridging portions 87 are multi-faceted and a cutting edge 89 is formed between two facets 90,91 which extends upwardly from each upright 86 towards a cutting tip at the apex 88 between the bridging portions 87. A further cutting edge 92 extends from the apex 88 of each U-shaped piercing element 85a,85b in a direction towards the other U-shaped piercing element 85a,85b associated with the same aperture 37,38.

Figure 27:
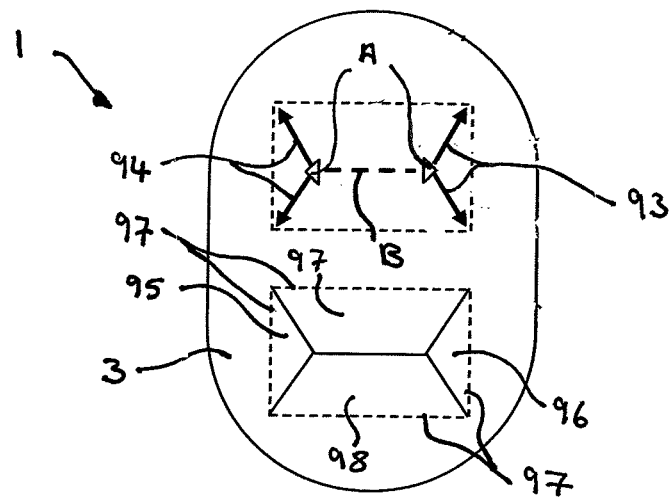
FIG. 27 shows a plan view of a blister lid to show the piercing pattern created using a piercing element illustrated in FIG. 26.

The cutting pattern produced in the lid 3 of a blister is illustrated in FIG. 27 from which it will be understood that the apex 88 of each piercing head makes an initial incision in the lid 3 as indicated by "A" in the drawing. Further insertion of the piercing heads into the blister causes the cutting edges 89 to cut slits 93,94 in the blister lid extending from the point of initial incision "A" outward towards the edge of the blister lid 3. It will be appreciated that there is essentially no cutting element extending between each pair of U-shaped piercing heads and so the blister lid 3 is burst open between the initial points of incision "A", as indicated by dashed line "B" in the drawing. As a consequence of slitting and bursting through the blister lid 3, two pairs of generally triangular or trapezoidal shaped flaps 95,96,97,98 are formed which are folded along fold-lines 97 into the blister 1 by the piercing heads during entry into the blister 1. Although there is no cutting element extending between each pair of piercing heads, it will be appreciated that cutting edge 92 fulfils the function of initiating a slit extending between the initial points of incision "A" prior to bursting.

Figure 28:
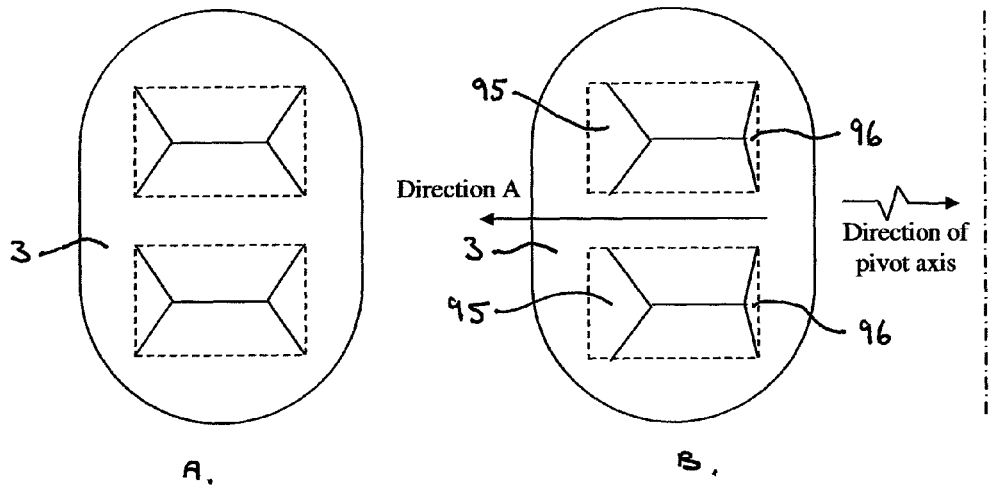
FIG. 28A shows a plan view of a blister lid illustrating a desired cutting pattern using the piercing element of FIG. 26.
FIG. 28B shows a plan view of a blister lid illustrating the actual cutting pattern using the piercing element of FIG. 26 when it is mounted to a pivoting actuator.

As has been described with reference to FIG. 16, the piercing element may be controlled so as to enter the blister 1 in a substantially linear path extending at right-angles to the plane of the blister lid 3. However, it is also envisaged that the piercing element may be mounted on a pivoting actuator (for example as disclosed in the Applicant's co-pending international application no. PCT/GB2004/004416 which has now been published as WO 2005/037353 A1) such that the piercing heads follow an arcuate path into a blister 1 and so approaches the lid 3 at a few degrees to the normal and has a component of movement in a direction parallel to the plane of the lid 3. In this case, use of the piercing heads described in the previous paragraph results in the flaps 95 furthest from the pivot axis being enlarged and, the flaps 96 closest to the pivot axis being reduced in size, as illustrated in FIG. 28B.

Figure 29:
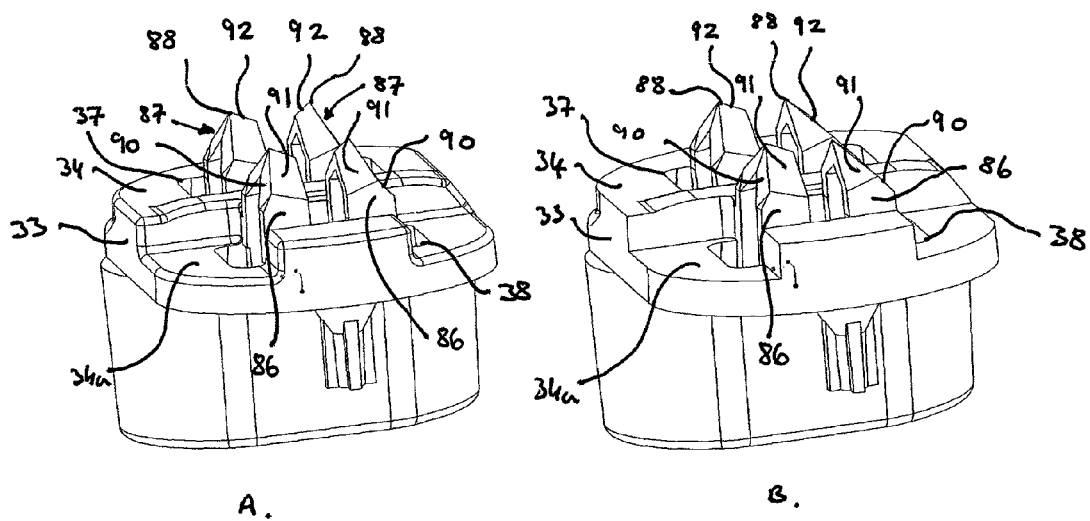
FIG. 29A to 29C show three modified versions of the piercing element shown in FIG. 26 to compensate for the angular approach of the piercing heads when mounted to a pivoting actuator with the aim of making the piercing pattern more closely resemble that shown in FIG. 28A.
Figure 29C:
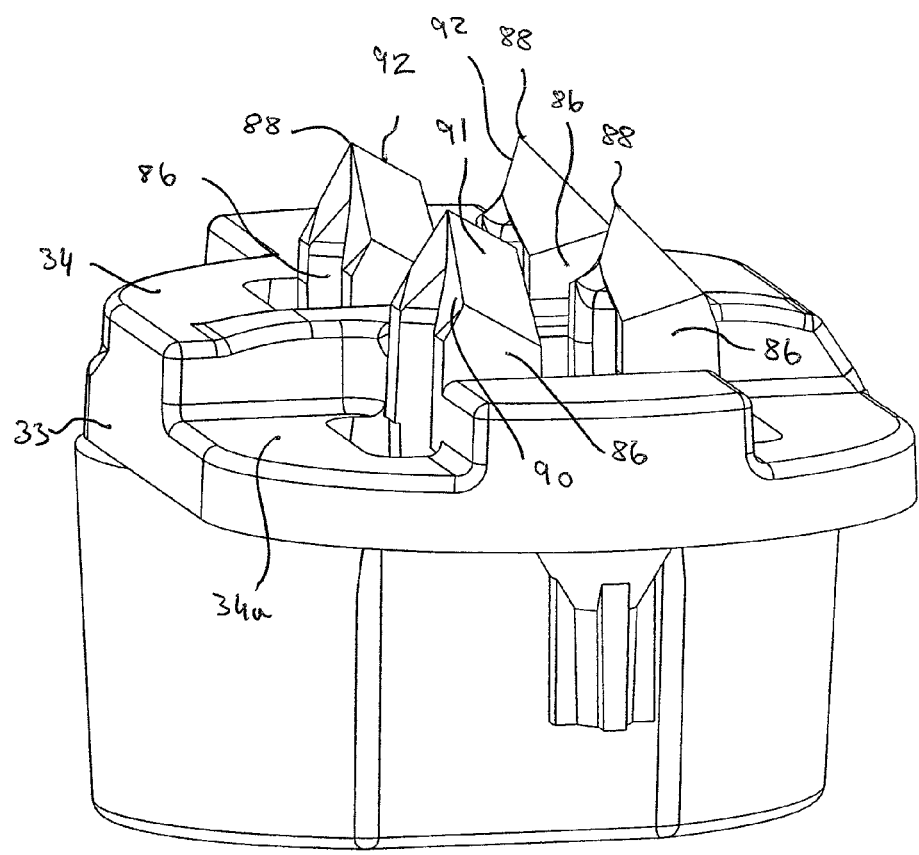

To compensate, a more pronounced chamfer can be provided to the facet extending from the cutting edge of the piercing elements closest to the pivot axis. However, care must be taken not to increase the chamfer too much as this can have a detrimental effect on the piercing pattern, leading to inconsistent piercing. Piercing elements having piercing heads with more pronounced chamfers are illustrated in FIGS. 29A, 29B and 29C. In FIG. 29A, the chamfer is pronounced to an intermediate stage whereas in FIG. 29B, the chamfer is fully pronounced.

In a preferred embodiment illustrated in FIG. 29C, the two facets 91 on the piercing elements closest to the pivot axis are twisted to form 3D curved surfaces that intersect to make a blade. The blade faces away from the pivot axis and in the direction of any component of movement in a direction parallel to the plane of the lid 3. The blade is angled at between 5 and 30 degrees and preferably between 10 and 20 degrees to the direction of protrusion of the piercing heads from their supports. In the embodiment of FIG. 29C the angle is 15 degrees. The blade meets the facets 90 at a point. During piercing this point makes an initial incision. The blade then enters the foil and ensures that the V-shaped slit necessary to achieve a repeatable burst during further piercing is maintained until the burst even when there is a component of movement parallel to the plane of the lid 3.

Figure 30:
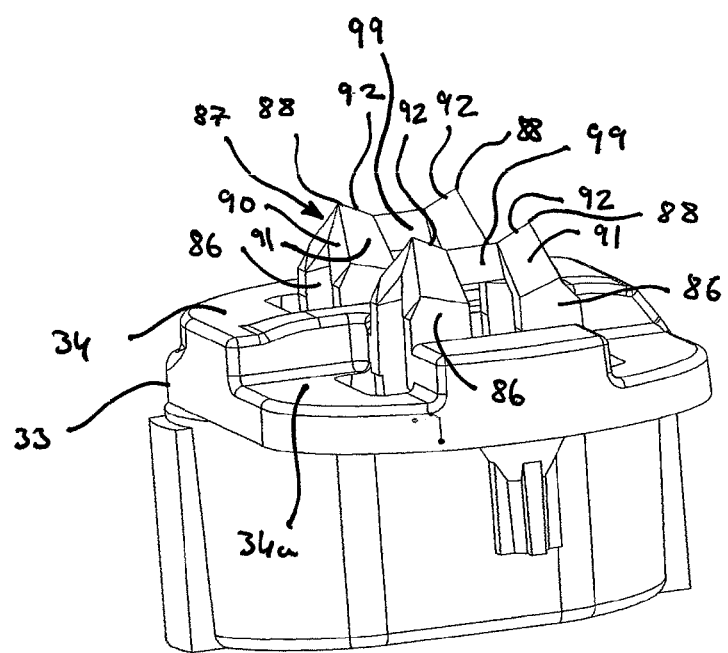
FIG. 30 shows another embodiment of piercing element according to the present invention.
Figure 31:
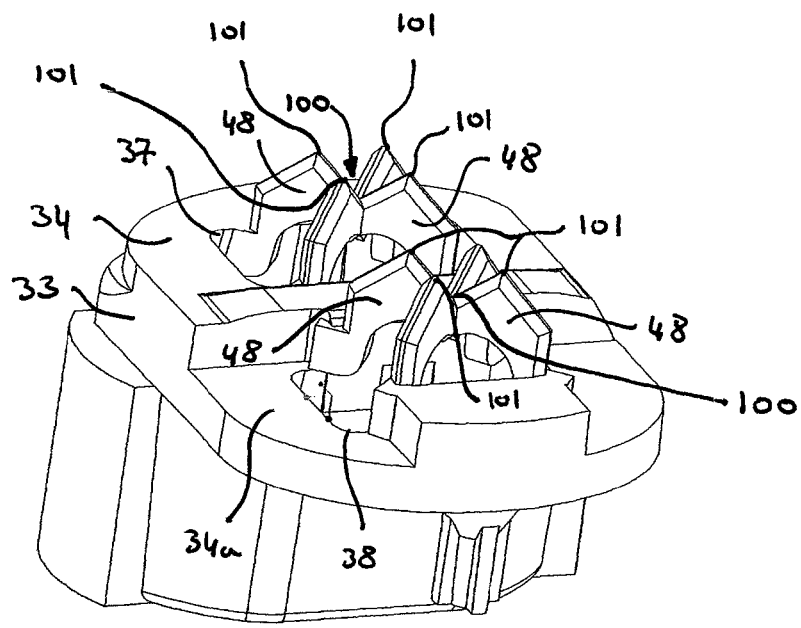
FIG. 31 shows yet another embodiment of piercing element according to an embodiment of the present invention.
Figure 32:
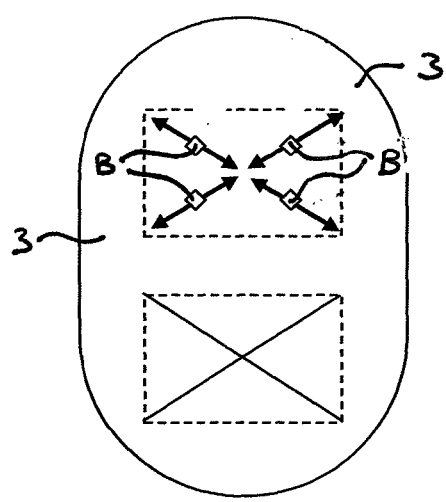
FIG. 32 shows a plan view of a blister lid to illustrate the cutting pattern formed by the piercing element of FIG. 31.

In a further variation of the aforementioned "double-U" shaped piercing head illustrated in FIG. 30, a bridge 99 extends between each pair of bridging portions 87. The bridge 99 acts to ensure that the bursting of the lid 3 between the initial points of incision marked "A" in FIG. 27 is achieved in a more precise and repeatable manner.

It is also envisaged that the bridge 99 need not extend fully between each pair of bridging portions 87 and may be attached to only one. The bridge 99 may have a generally curved peripheral surface, i.e. it could be cylindrical so that it bursts through the lid 3 as opposed to cutting it. It will also be appreciated that the bridge 99 is located beneath the apex 88 of the bridging portions 87 so that an initial incision and slits are cut by the cutting edges 92 prior to contact of the bridge 99 with the lid 3. As mentioned above initial slits are cut in the lid 3 between the two points of initial incision "A" by cutting edges 92 to facilitate a controlled bursting through the lid 3 by the bridge 99.

A second development of the envelope type piercing element, known as the "double cross" type piercer will now be described with reference to FIGS. 31 to 36.

It has previously been mentioned, in relation to the embodiment of FIGS. 14 and 15, that the length of the primary cutting tooth 50 extending between the secondary cutting teeth 48 can be varied to the extent that the primary and secondary cutting teeth 48,50 substantially form an "X" shape in plan view.

In the present embodiment, the primary cutting tooth 50 is omitted altogether so that the secondary cutting teeth 48 all meet at the same apex 100, as shown in FIG. 30.

Each cutting tooth 48 tapers to a pointed cutting tip 101 together they produce a four substantially triangular flaps, each of a similar shape and size. Each cutting tooth 48 cuts from an initial insertion point (marked "B" in two opposite directions towards the apex and away from it towards the outer edges of the blister lid 3, as shown by the arrows in FIG. 32. This makes for more consistent, controlled piercing of the blister lid 3.

The starting point for cuts in the blister lid 3 is ideally towards the outer edges of the blister 1 for optimum cutting where the lid 3 is better supported. However, in order to allow the piercer to enter the blister 1 fully, it may be advantageous to move the starting point for the cuts up to half way towards the centre of the lid to allow the points to fit into the blister 1 after piercing i.e. so that the cutting tips 101 enter the blister 1 towards its deepest point.

Figure 33:
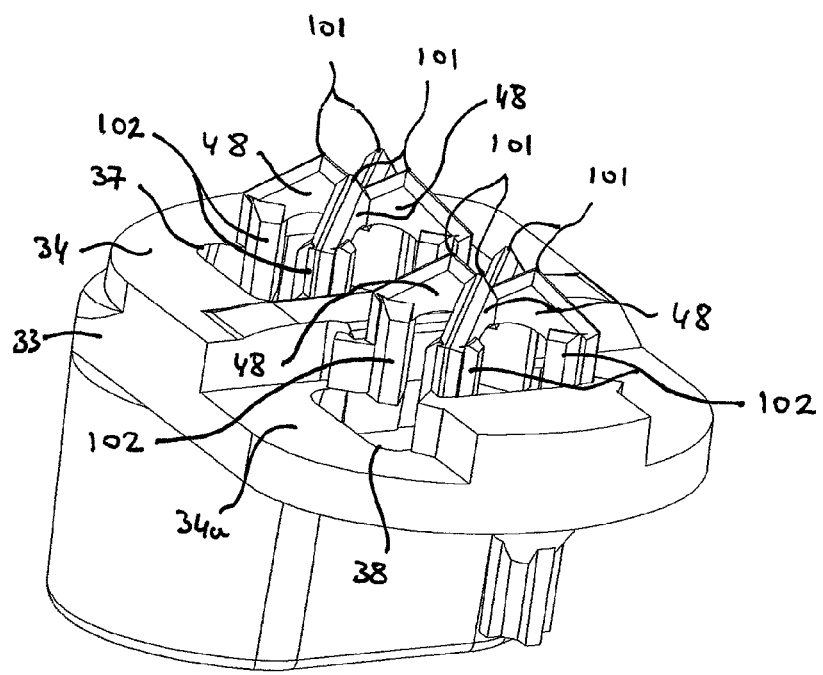
FIG. 33 is a modified version of the piercing element shown in FIG. 31.
Figure 34:
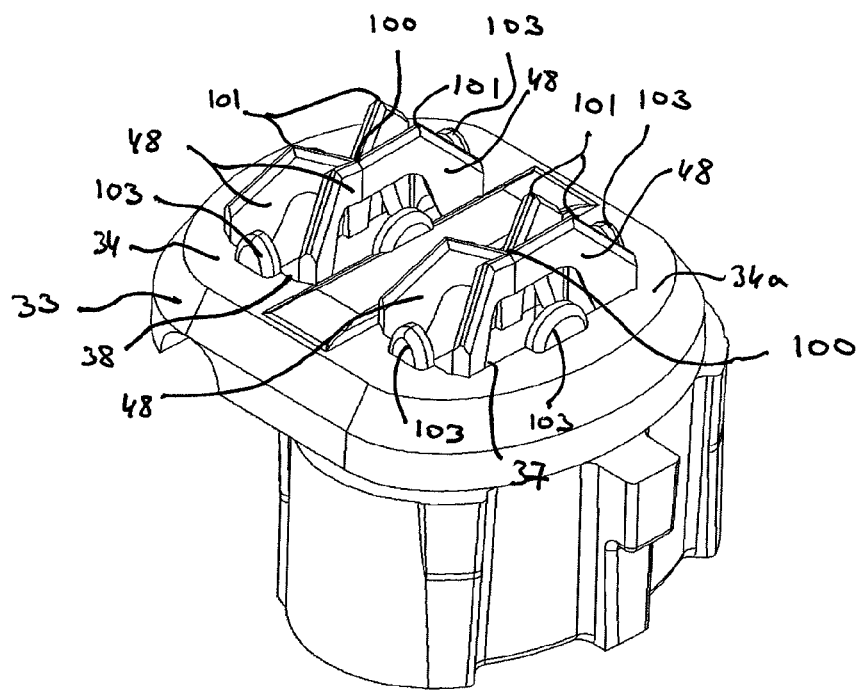
FIG. 34 is another modified version of the piercing element shown in FIG. 31.

In a modification of the above-described piercing element, illustrated in FIG. 33, the piercing teeth 48 have a widened portion 102 near their root to facilitate opening of the flaps during piercing. In yet another modification, as shown in FIG. 34, nodes or other protruberances 103 upstand from the surface 34, 34a of the piercing head between the cutting teeth 48 and from the periphery of the apertures 37,38 which aid in pushing open the flaps during piercing.

Figure 35:
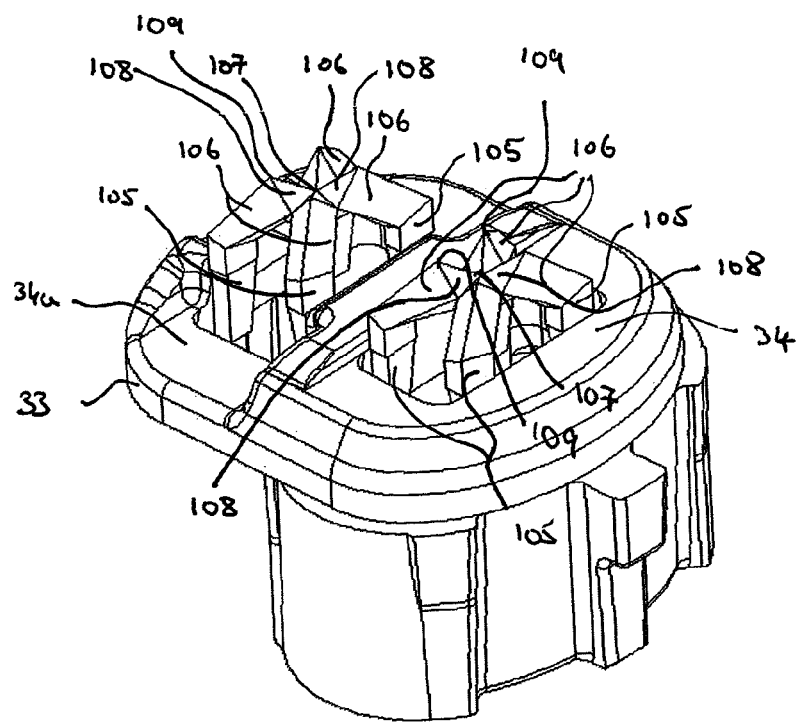
FIG. 35 is yet another embodiment of piercing element according to an embodiment of the present invention.
Figure 36:
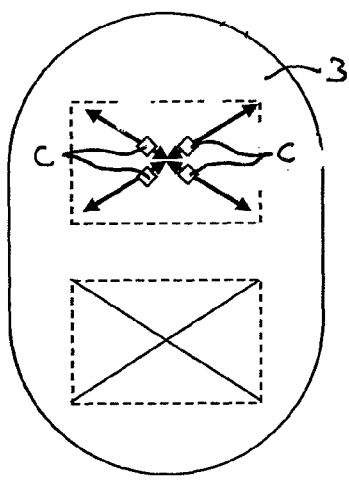
FIG. 36 is a plan view of a blister lid to illustrate the cutting pattern formed by the piercing element of FIG. 35.

A final embodiment is called the "four point crown" piercing element and is illustrated in FIG. 35. This embodiment is essentially a combination of the double U-type piercing element shown in FIG. 26 and, the double cross type piercing element shown in FIG. 30 and comprises four uprights 105 extending from the surface 34,34a. An arm 106 extends angularly inward and upward from the end of each upright 105 and meets at an apex 107. The end of each arm 106 is cut away to form four triangular shaped facets 108 each having a pointed tip 109. These tips 109 initiate four incisions in the blister lid very close to the centre of the lid (see incisions marked "C" in FIG. 36) and each cutting tooth then cuts a slit in the lid extending outwardly and inwardly from each incision.

Many modifications and variations of the invention falling within the terms of the following claims will be apparent to those skilled in the art and the foregoing description should be regarded as a description of the preferred embodiments only.

The invention claimed is:

1. A blister piercing element for puncturing the lid of a blister containing a dose of medicament for inhalation by a user, the piercing element comprising a body portion having a planar surface that lies flush against a surface of a lid of a punctured blister when the blister piercing element has fully entered the blister, a planar outlet opening in said planar surface having planar inner walls that form the opening for the passage of medicament entrained in an airflow out of the blister, and a piercing head having a first portion extending perpendicularly, or substantially perpendicularly from said planar surface and a second portion having an end remote from said first portion, said piercing head being L shaped in side elevation, with the first portion upstanding from a periphery of the planar outlet opening and the second portion extending in a more lateral direction across and overhanging the planar outlet opening such that the second portion cuts a flap in a lid of a blister and pushes it away from the planar outlet opening during insertion through said lid, said second portion extending laterally away from an end of the first portion wherein the second portion comprises a primary cutting edge formed at said remote end of the second portion, the second portion also comprising a pair of secondary cutting edges, each secondary cutting edge extending from the primary cutting edge, the primary cutting edge being remote from said planar surface and from said first portion and having a tip at one end, the primary cutting edge being angled relative to the plane of a blister lid in such that only said tip initially meets the blister lid to initiate a slit in the lid.

2. A blister piercing element according to claim 1, wherein the piercing head extends from a portion of the periphery of the outlet opening.

3. A blister piercing element according to claim 1, wherein a portion of the primary cutting edge remote from the tip is chamfered or otherwise removed.

4. A blister piercing element according to claim 1 comprising an inlet opening and a further piercing head, said further piercing head extending beyond and overhanging the planar inlet opening.

5. A blister piercing element according to claim 4, wherein the piercing heads are arranged in a back-to-back configuration.

6. A blister piercing element according to claim 4, wherein the piercing heads are spaced from each other in a first direction and offset from each other in a lateral direction at right angles to said first direction.

7. A blister piercing element according to claim 4, wherein the primary cutting edge of each piercing head is angled so that the cutting tip initiates an incision close to the centre of a blister lid and the secondary cutting edges cut a slit in the blister lid in opposite outwardly extending directions towards opposite edges of the blister lid.

* * * * *